(12) United States Patent
Lizotte et al.

(10) Patent No.: US 7,668,364 B2
(45) Date of Patent: Feb. 23, 2010

(54) INSPECTION METHOD AND APPARATUS FOR PARTIALLY DRILLED MICROVIAS

(75) Inventors: Todd E. Lizotte, Manchester, NH (US); Orest Ohar, Hooksett, NH (US)

(73) Assignee: Hitachi Via Mechanics, Ltd., Kanagawa (JP)

( * ) Notice: Subject to any disclaimer, the term of this patent is extended or adjusted under 35 U.S.C. 154(b) by 681 days.

(21) Appl. No.: 11/411,977

(22) Filed: Apr. 26, 2006

(65) Prior Publication Data

US 2008/0144921 A1 Jun. 19, 2008

Related U.S. Application Data

(60) Provisional application No. 60/674,752, filed on Apr. 26, 2005.

(51) Int. Cl.
*G06K 9/00* (2006.01)

(52) U.S. Cl. ........................ 382/141; 382/209

(58) Field of Classification Search ............ 382/141, 382/144, 145, 152, 153, 209
See application file for complete search history.

(56) References Cited

U.S. PATENT DOCUMENTS

| | | | | |
|---|---|---|---|---|
| 6,172,329 B1 * | 1/2001 | Shoemaker et al. | .... | 219/121.69 |
| 6,236,033 B1 * | 5/2001 | Ebbesen et al. | ............. | 250/216 |
| 6,531,677 B2 * | 3/2003 | Arai et al. | ............. | 219/121.71 |
| 6,621,572 B2 * | 9/2003 | Savareigo | ................. | 356/237.5 |
| 6,690,024 B1 * | 2/2004 | Funaoka et al. | ........ | 250/559.45 |
| 6,697,154 B2 * | 2/2004 | Owen et al. | .............. | 356/237.5 |
| 6,791,060 B2 * | 9/2004 | Dunsky et al. | ........... | 219/121.7 |
| 7,062,354 B2 * | 6/2006 | Ganot et al. | ................. | 700/192 |
| 7,205,501 B2 * | 4/2007 | Arai et al. | ................. | 219/121.7 |
| 7,271,877 B2 * | 9/2007 | Fries | ........................... | 355/67 |
| 7,283,660 B2 * | 10/2007 | Ganot et al. | ................. | 382/151 |
| 2002/0027654 A1 * | 3/2002 | Owen et al. | ............... | 356/237.5 |
| 2003/0190071 A1 * | 10/2003 | Ganot et al. | ................. | 382/151 |
| 2003/0213787 A1 * | 11/2003 | Dunsky et al. | ......... | 219/121.75 |
| 2004/0081351 A1 * | 4/2004 | Ganot et al. | ................. | 382/151 |
| 2008/0144921 A1 * | 6/2008 | Lizotte et al. | ............... | 382/145 |

* cited by examiner

*Primary Examiner*—Gregory M Desire
(74) *Attorney, Agent, or Firm*—Davis & Bujold, P.L.L.C.

(57) ABSTRACT

Inspection of partially drilled microvias by fluorescence based optical imaging techniques, selective coaxial illumination and multivariable off-axis illumination and the use of comparative image analysis and the transformation of back reflected radiation by means of an integrated fluorescing plate mounted to the surface of a CCD or EMCCD array.

2 Claims, 24 Drawing Sheets

FIG. 19  Fluorescent Glass Substrates (UV to Visible Transforming)
Ultraviolet @355 nm transformed to 542 nm emission
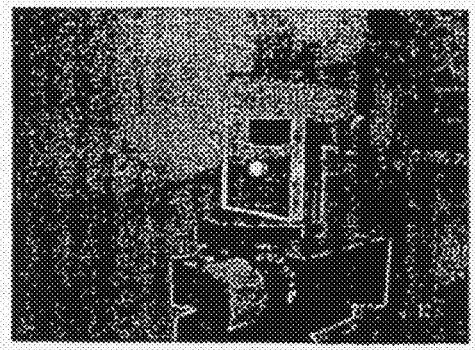
Ultraviolet @355 nm transformed to 612 nm emission
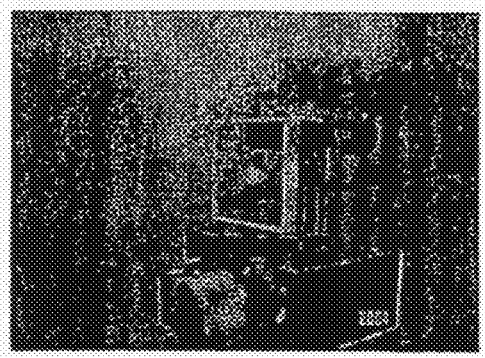
Ultraviolet @355 nm transformed to 405 nm emission
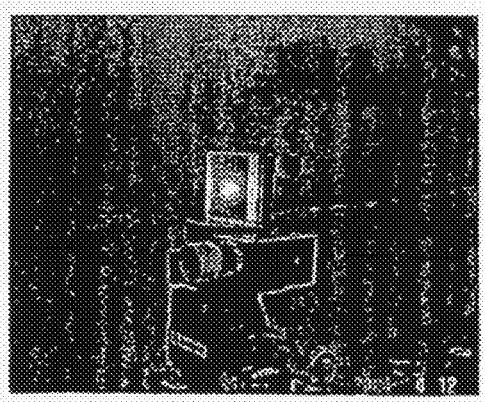

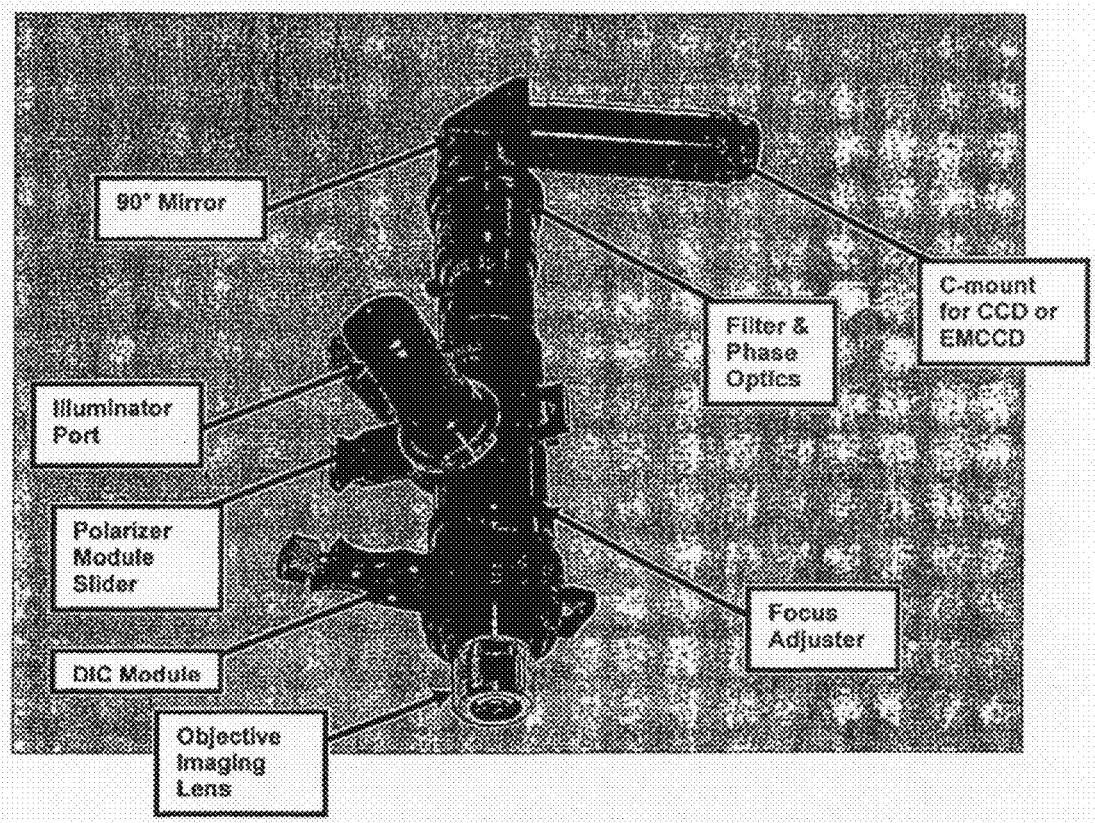
FIG. 22 Fluorescent Differential Interference Phase Contrast Imaging System 45 micron microvia / large taper bottom of hole / remianing polymer
Fluorescent image of the polymer Color enhanced image created using scope setup from Figure 6

Gray scale image created using scope setup from Figure 6

INSPECTION METHOD AND APPARATUS FOR PARTIALLY DRILLED MICROVIAS

CROSS REFERENCES TO RELATED APPLICATIONS

The present application is related to and claims benefit of Provisional Patent Application Ser. No. 60/674,752 filed Apr. 26, 2005 by Todd E. Lizotte and Orest P. Ohar.

FIELD OF THE INVENTION

The present invention relates to a method and an apparatus for inspection of partially drilled microvias by fluorescence based optical imaging techniques, selective coaxial illumination, multivariable off axis illumination and using comparative image analysis and transforming of back reflected radiation by means of an integrated fluorescing plate mounted to the surface of a CCD or EMCCD imaging array.

BACKGROUND OF THE INVENTION

Current automatic optical inspection (AOI) systems use standard illumination, optical imaging techniques and filters to differentiate the features being inspected to the surrounding bulk material.

When AOI is applied to the task of inspecting a laser microvia that is 50 microns in diameter and below, standard AOI systems fail to perform. Standard AOI equipment lack the resolution and capability to differentiate the conductor pad which is supposed to be exposed and free from any contaminants, when the top dielectric is removed as the laser beam drills down to the conductor pad.

The typical rejected microvia is one that has remaining thin film of dielectric on the surface of the conductor pad. This remaining thin film of dielectric can take the form of what is defined as smear, or left over material, either it be adhesive, polymer, glass or resin. If the AOI system fails to find partially removed dielectric at the bottom of a microvia, even the slightest amount of dielectric film or resin, the microvia when plated or filled with a conductor will short or electrically fail once the product is delivered to clients.

Standard AOI systems are limited in the viewing of microvias, since microvias typically have diameters down to 10 microns. This leaves few options for lighting and differentiating these thin films. In many cases the AOI systems do not even detect the thin film that can be a thin as 1 micron. In short the AOI systems have an unacceptable rate of false positives which leads to yield issues once more value is added to the multilayered printed circuit board or flex circuit. In the case of high density chip packaging, one failure could cause serious failures in the field if the microvia is partially drilled. In many cases next generation chip packaging will have nearly 40,000 microvias per chip package, only a few faulty microvias can ruin a product.

SUMMARY OF THE INVENTION

The present invention is directed to a method and apparatus for inspection of partially drilled microvias by fluorescence based optical imaging techniques, selective coaxial illumination and multivariable off-axis illumination and the use of comparative image analysis and the transformation of back reflected radiation by means of an integrated fluorescing plate mounted to the surface of a CCD or EMCCD array.

The present invention utilizes the fluorescent nature of polymers and the differentiating of this fluorescence from the bulk surrounding material by uniquely illuminating only the area of interest for inspection, used in the manufacture of multilayered printed circuit boards and flex circuits used to create chip packages and other computer PCB products.

The present invention also covers the use of multiple frame images of varying illumination and optical imaging technique to create levels of redundancy to ensure that false positives and false negative do not occur.

The present invention describes that the use of coaxial illumination in conjunction with off-axis provides a means to further differentiate the bulk surrounding material form the area being inspected.

The invention also emphasizes the tailoring of the coaxial illumination to illuminate the conductor pad or the selected area to be inspected. This type of selective illumination provides a better signal to noise ratio, since the surrounding bulk material is limited in illumination and will not add to the signal. The present invention also provides for the simultaneous use of multiple wavelength which can simultaneously enhance various features to further isolate the defects for proper inspection and analysis.

The present invention disclosure also covers the use of fluorescence formed at the CCD "Charged Coupled Device" or EMCCD "Electron Multiplied Charged Couple Device" array by use of back reflected light from a UV or other illuminator source which is imaged onto a fluorescent glass plate mounted to the surface of the CCD or EMCCD.

BRIEF DESCRIPTION OF THE DRAWINGS

FIG. 19 illustrates types of fluorescent glass plates illuminated by UV light;

FIG. 22 illustrates a system of the present invention; and,

DESCRIPTION OF THE INVENTION

Figure 1:
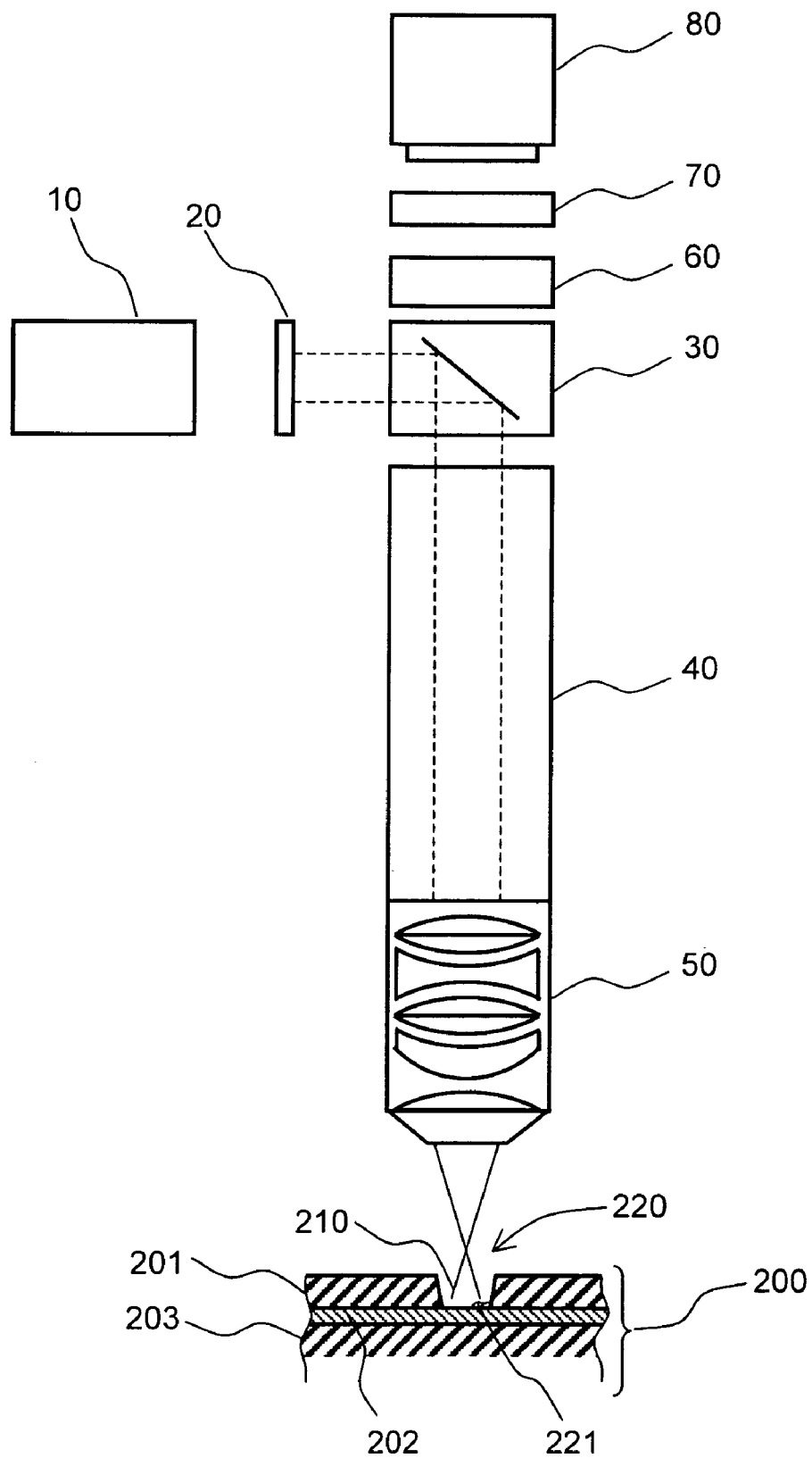
FIG. 1 illustrates a basic system that can image the defects by the use of the fluorescence emission.

FIG. 1 shows a basic system that can image the defects by the use of the fluorescence emission.

The first approach uses a standard CCD and/or an EMCCD (hereinafter, simply referred to as "CCD") 80. The use of a EMCCD or a L3CCD "Low Light Level CCD" provides a means to image very low fluorescent emissions from polymers being illuminated by an appropriate excitation wavelength. This system is optimized for higher sensitivity, faster speed, enabling lower concentrations of emitting molecules to be detected with shorter exposure times and lower excitation powers. The CCD 80 is coupled to a series of optical elements (filters) 70 including a UV filter or a specific filter for the illuminator wavelength or a stack of filters to isolate the wavelength of light being emitted by the polymer being illuminated.

The next stage is conditioning optics 60 to transfer the image to the CCD 80. This optic provides added capability to condition the image formed by the emission of fluorescence of the targeted dielectric film 201.

A key element of the system is the use of a computer generated hologram "CGH" or a diffractive based beam shaper 20 from the illuminator 10 being used to excite the dielectric film 201 or material 221 on the surface of the microvia conductor pad. By shaping the illumination beam the CGH or Diffractive Optical Element "DOE" (hereinafter, referred to as "beam shaper") 20 can shape the illuminator beam into a uniform circular profile to a size that is smaller than the base microvia 220 diameter which is critical. By shaping the illumination so that it illuminates only the area under investigation, the process becomes very selective and more stabile. Other techniques that use fluorescence flood illuminate from an off-axis basis and do not have a uniform profile. This leads to fluorescence by the bulk material creating further complications to differentiate the area under analysis from the bulk material.

By using a beam shaper 20 to shape the beam and provide the shaped beam collinear to the imaging system "on axis" the excitation illuminator light can be of less power.

The illuminators shaped beam is directed down through the scope by using a beam splitter 30 that is set coaxially with the scope system.

The shaped illuminator beam 210 is then delivered to the surface by the multi-element imaging objective lens 50 which in turn images the fluorescence onto the CCD array 80 surface. By using filters 70 the CCD 80 can be shown just the emission spectra of the dielectric under observation.

Figure 2A:
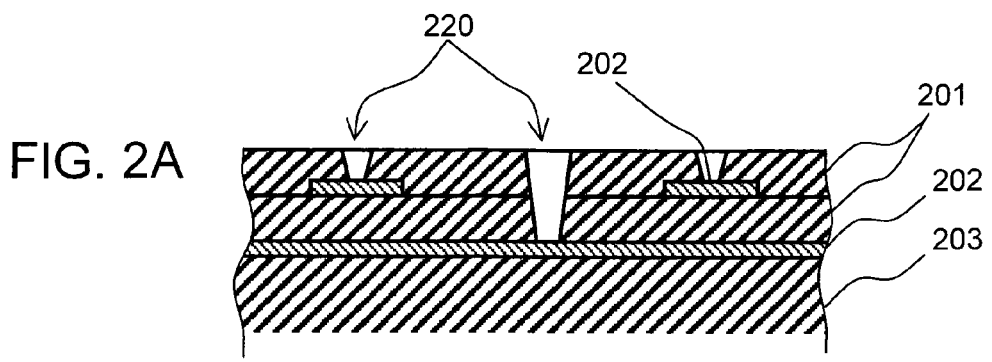
FIG. 2A is a schematic cross section of a multilayered printed circuit board or flex circuit.
Figure 2B:
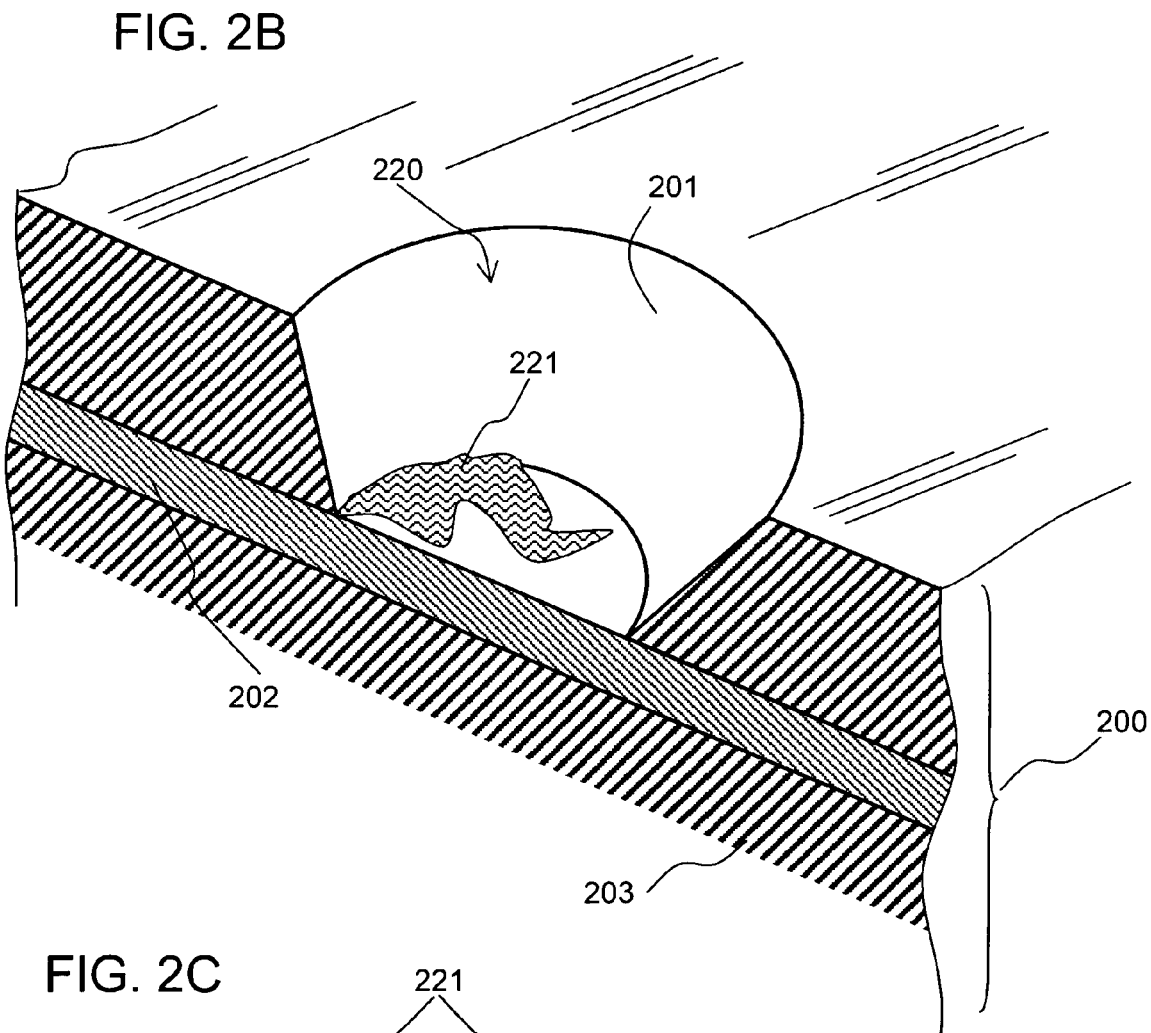
FIGS. 2B and 2C is a perspective sectional view and a cross section of a laser drilled microvia with a smear, respectively.
Figure 2C:
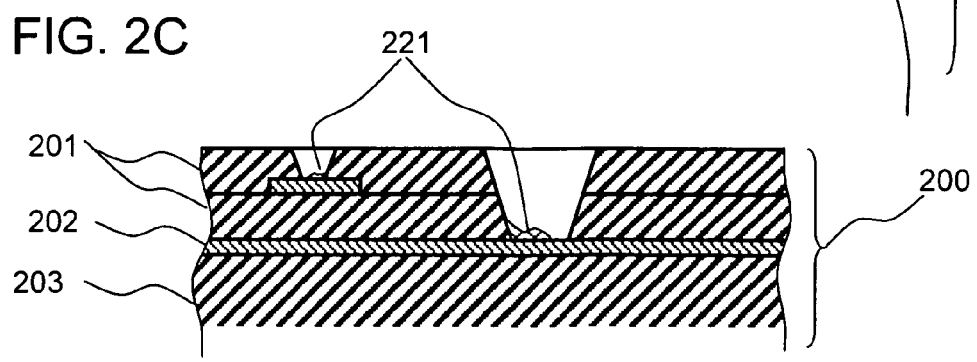

FIG. 2A shows in schematic form how microvias 220 look in cross section on a multilayered printed circuit board or flex circuit. A copper (or other) conductor layer 202 is laminated to a dielectric or (FR4) PCB board or a flexible dielectric (hereinafter, simply referred to as "dielectric") 203, then a dielectric or dry film or resin layer (hereinafter, referred to as "dielectric layer") 201 is laminated to the conductor layer 202. Then another conductor layer 202 is laminated to the dielectric layer 201 and formed to pads by etching or the like. After that, another dielectric layer 201 is laminated, then the microvias 220 are drilled by laser. FIGS. 2B and 2C show a cross section of a microvia hole 220, showing what left over dielectric defect 221 might look like. It should be understood, that the use of fluorescence can also detect if the laser damaged the conductor 202, by blowing through it in select locations. This type of defect is also of concern, especially when dealing with thin layer conductors or bad adhesion characteristic of conductors.

Figure 3:
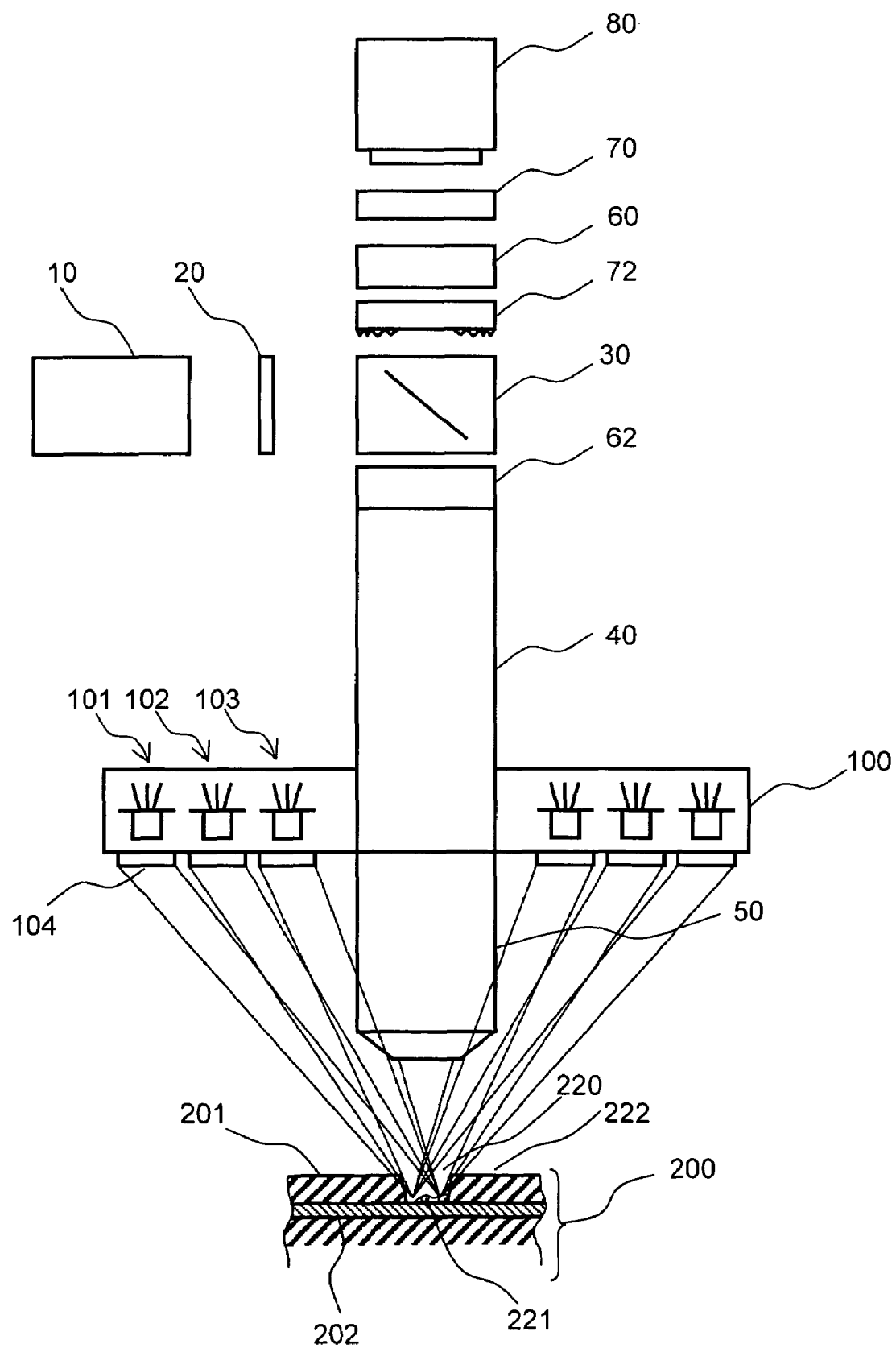
FIG. 3 illustrates a non-coaxial illuminator system.

FIG. 3 shows a non-coaxial approach where a ring illuminator 100 of varying wavelength illuminators can simultaneously illuminate the microvia 220 from all sides. The ring illuminator 100 has IR LEDs 101, UV LEDs 102 and visible LEDs 103, and beam shapers 104 in 360 degrees around the imaging lens 50. These LEDs illuminates the microvia 220 overlappingly with shaped uniform beams. A UV or other light source can be used as the illuminator 10 in this case, such as laser diode, DPSS laser, UV lamp, IR LED or visible LED. Although this floods the bulk material 222 around the microvia 220, the varying of different illumination wavelengths allows the bulk surrounding material 222 to be isolated by a method of multi-frame compilation analysis technique that is used to ensure that what is being detected is truly being scene. This technique of multiple image comparison/compiling is shown schematically in FIGS. 11 & 12 and described later.

FIG. 3 shows a non-coaxial illuminator design as mentioned above, but it also has a unique item to minimize bulk emission in the image formed on the CCD array 80. This item is a diffractive aperture 72 which is sized to the feature being inspected. The diffractive or computer generated hologram diverges the incoming bulk peripheral emission signal generated by the bulk material 222 surrounding the microvia 220 or feature being inspected. This is particularly useful in reducing the signal to noise ratio, so to emphasize the emission from the defects being identified. By diverting the outer signal before it floods the CCD 80, ensures that the CCD 80 is focused on the area of interest 220 rather than the bulk material 222 surrounding the area of interest 220.

With regard to the above, transfer optics are used in conjunction with the imaging objective under certain circumstances, such as to improve the image, improve chromatic errors, and so on. On tube scope systems, for example, transfer optics are sometimes referred to as auxiliary lenses and allow modification of the field of view or of the numerical aperture (NA).

Figure 4:
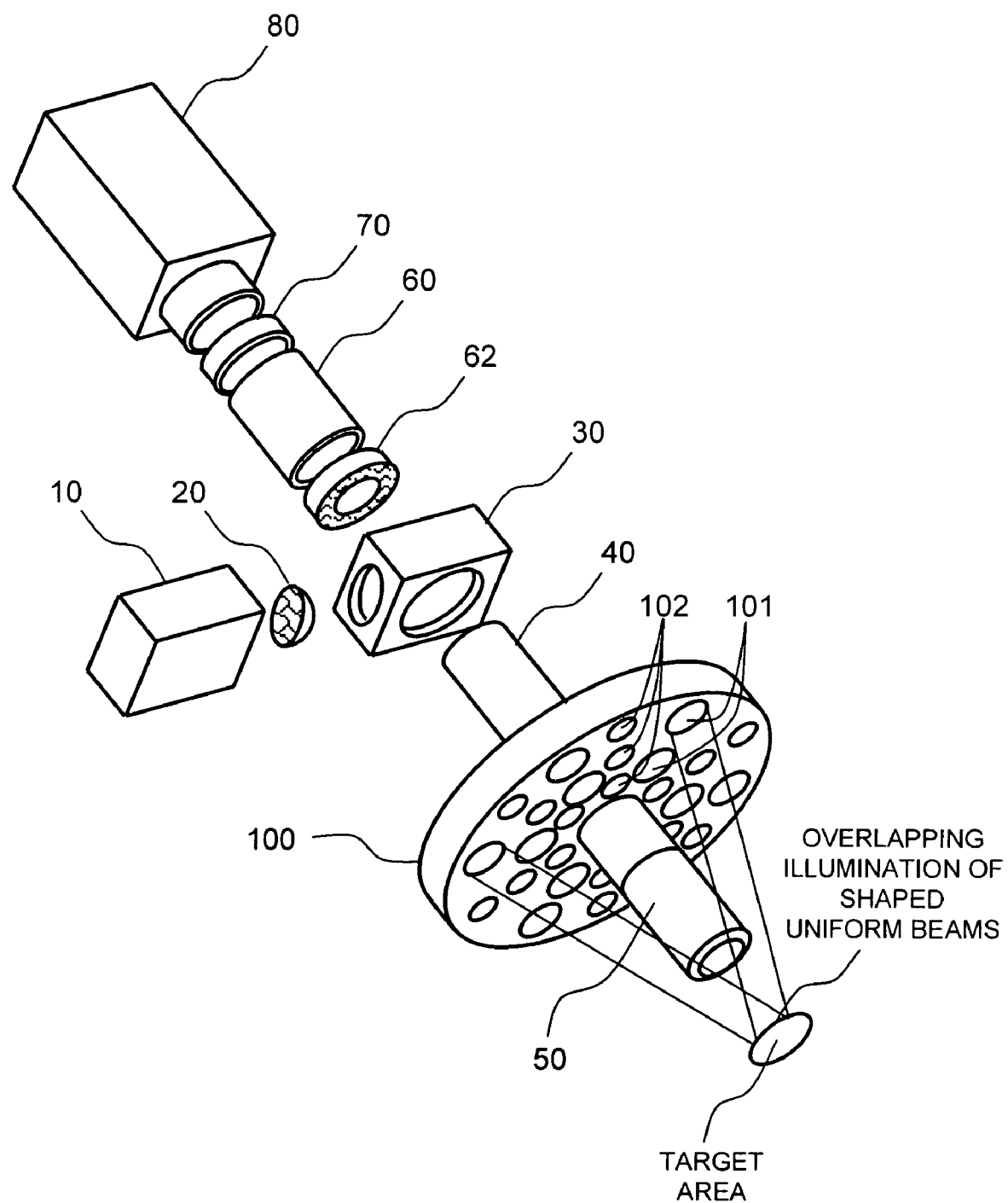
FIG. 4 illustrates an imaging scope setup where the system uses both coaxial and off axis illumination to illuminate the feature or microvia being inspected.

FIG. 4 shows an imaging scope setup where the system uses both coaxial and off axis illumination to illuminate the feature or microvia being inspected. The coaxial illuminator 10 is at a wavelength specific to the defects or left over material residing at the bottom of the microvia or feature being inspected and the off axis illuminators 100 are selected to minimize the impact of the surrounding bulk material or to enhance the areas on the conductor pads that are exposed, relative to the areas which have left over dielectric or other contaminants. The use of dual coaxial/off axis illumination provides a substantial benefit over either or designs. First, the coaxial 10 allow specific illumination to the contaminated area or area of interest for finding defects. This allows the vision acquisition system as well as the CCD 80 to concentrate on what is important. By highly selective illumination of the area of interest, i.e. area where contamination or defects or left over dielectric might reside, minimizes processor time for analysis, creating a more efficient system overall. By combining the two techniques, the system has the ability to take a series of image frames and apply compilation, overlay, and image "go/no go to known standard" comparison methods of analysis to provide a high level of accuracy over traditional blob analysis. This also allows the use of multiple wavelengths of illumination allowing the coaxial to be at the best wavelength for the defects or left over material of interest, and the off axis illumination wavelength is optimized for the specific surrounding bulk material or to emphasize the area being inspected that have no defects, i.e. the conductor pad that is clean. This dual approach offers greater imaging and inspection advantages for complex material combinations, including differing dielectric layers, different conductor types (Au, Cu, At, etc), specialize coatings, etc.

Figure 5A:
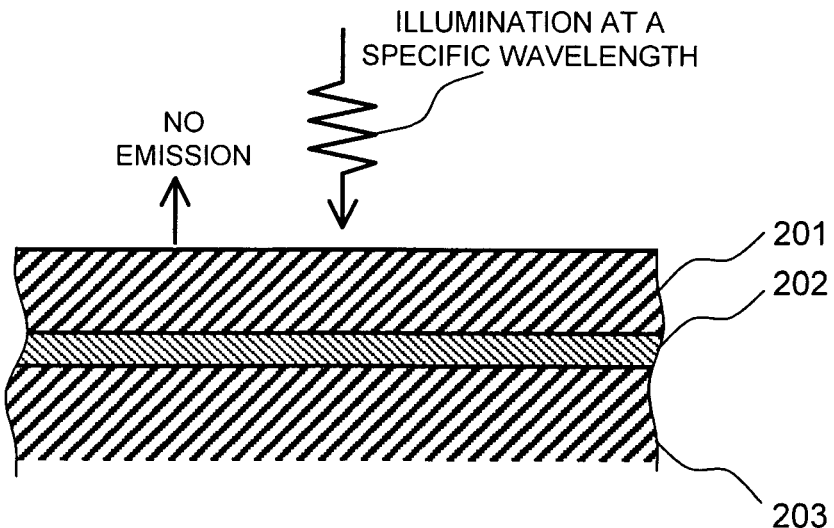
FIGS. 5A, 5B and 5C show in schematic form how a material reacts when illuminated by a specific wavelength.
Figure 5B:
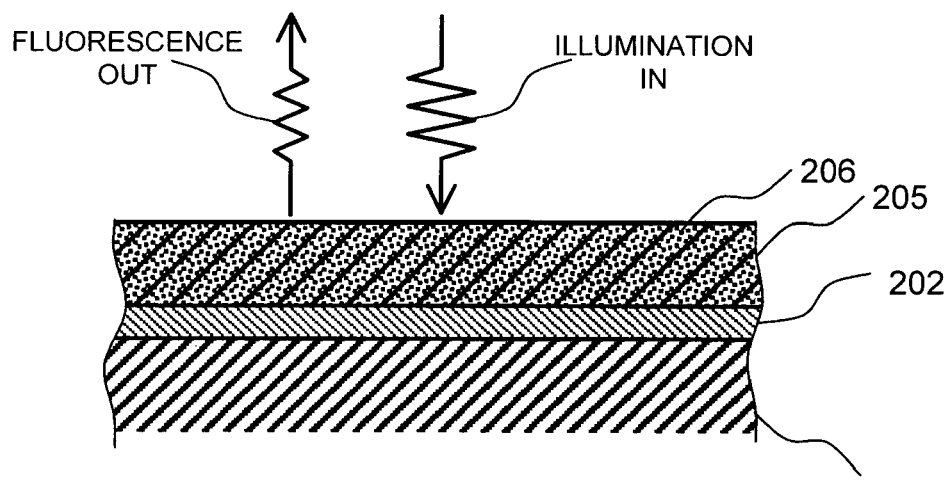
Figure 5C:
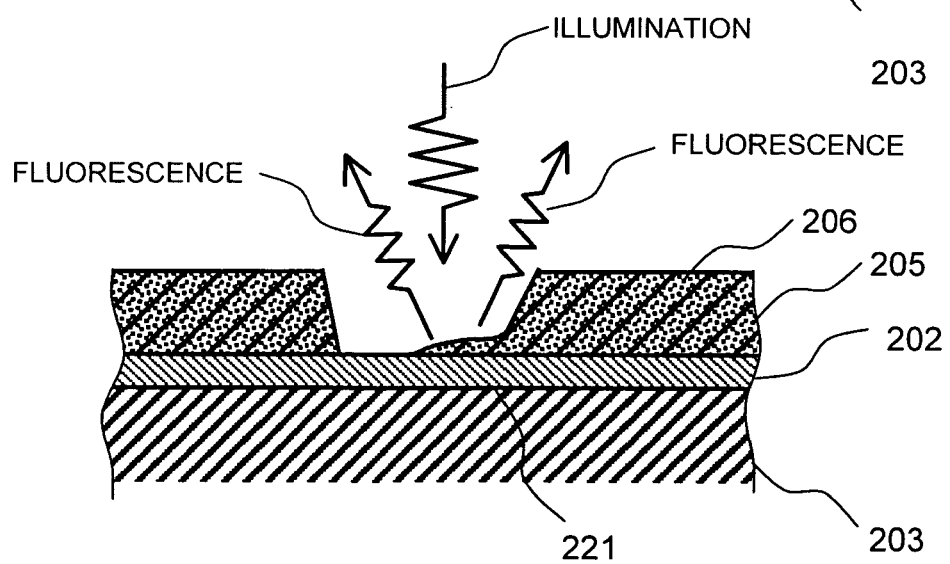

FIGS. 5A, 5B and 5C show in schematic form how a material reacts when illuminated by a specific wavelength. FIG. 5A shows how no emission is generated when the polymer has not fluorescence capabilities. FIG. 5B shows how the addition of fluorescent dopants or dyes 206 in small quantities in dielectric layers 201 could allow the material to fluoresce under illumination by a specific wavelength of illumination. FIG. 5C shows how these dopants or dyes 206 can enhance the detection of thin film dielectric layers 201 which form defects (smear) 221 at the conductor pad surface. These left over films 221 of dielectric are produced by partially drilled laser microvias.

With regard to the above, it should be noted that some polymers have natural fluorescence capability and would therefore often not require dopants. For example, general epoxies used within the PCB industry tend to fluoresce in the yellow to green and certain of these epoxies do not need dopants at all if there is a natural fluorescence that is emitted when these polymers are illuminated by UV radiation. In the case of glass fiber reinforced substrates, special coatings, for example, Dansyl which is used to treat the glass fibers to provide better adhesion to the epoxy matrix, improves the fluorescence of the glass fiber/epoxy interface. Other materials, such as fluorescent dyes (fluorochromes) can be used, and an example of a good dye for reaction with UV light is Hostasol Red GG and Hostasol Yellow 3G. However depending on what is to be observed, dyes are necessary only to enhance the imaging.

Figure 6:
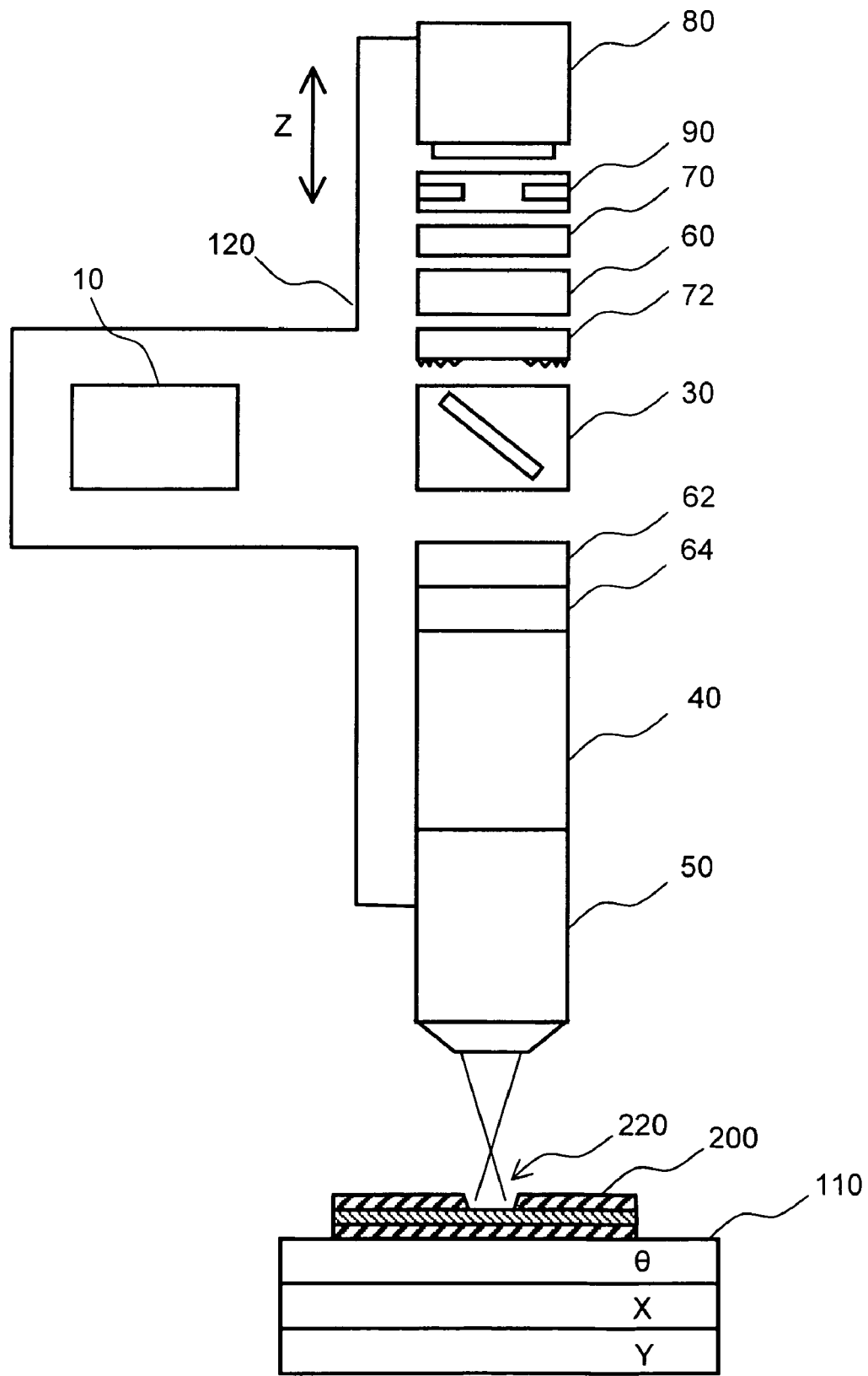
FIG. 6 illustrates another coaxial illuminator system.

FIG. 6 incorporates another useful set of tools within the coaxial system, a polarizer 64 in conjunction with a combined high speed filter and indexing aperture wheel (indexing filter and aperture wheel) 90 of the type generally well known in the art. These devices allow for further differentiation of defects being observed from the bulk material or to differentiate the defects or thin left over dielectric film from the conductor pad. The scope system is mounted on a Z focus stage 120 and a PCB to be inspected is mounted on an X-Y-Z stage 110.

With regard to the indexing filter and aperture wheel discussed above that above, it should be noted that under certain conditions it is advantageous to limit the amount of light entering into the camera. This can be achieved by using an iris or fixed aperture to limit this light. Under other circumstances it is better to use a band pass filter or a narrow pass filter which limits specific wavelength of light or even use a neutral density filter to reduce the intensity of the image on the camera.

With regard to the filter for back reflected illuminator wavelength it should be noted that the back reflected filter is a band pass filter. For example, if the surface is illuminated with a UV light at 405 nanometers and the fluorescent signal generated by the material is at 450 to 500 nanometers, it is necessary to only allow the 450 nm to 500 nm light to reach the camera. It is therefore possible to use a band pass filter which allows only the wavelength between 450 to 500 nm get to the camera. It should also be noted that 450 nm to 500 nm is only one of the possible ranges of fluorescence that can be employed and that different dyes would provide different fluorescence emission frequencies. For example, the fluorescence wavelengths may lie in the red portions of the spectrum and the green range frequencies are often easier to view using standard CCD technology With regard to the back scatter filter (HOE/DOE) it should be noted that this element is a substrate which has a clear central aperture, with a diffractive structure surrounding the clear aperture. The diffractive structure re-directs the light away from the central inspection zone being imaged. This allows a larger field of view for inspection, larger illumination zone, but allows the system to reject bulk noise that is not necessary for the inspection, i.e. the fluorescence surrounding the microvia being inspected, it offers a method to improve the signal to noise ratio when inspecting.

It should also be noted with regard to the variable auto adjustable polarizers that polarization offers advantages by enhancing the image, depending on what aspects for the image are of interest. In this case, polarization assists in clarifying the image and the polarization is configured in this system to allow for an automatic adjustment. The system has two polarizers that can be adjusted relative to each other automatically according to the inspection criteria. The polarizers are counter rotated to allow for variable polarization.

Figure 7A:
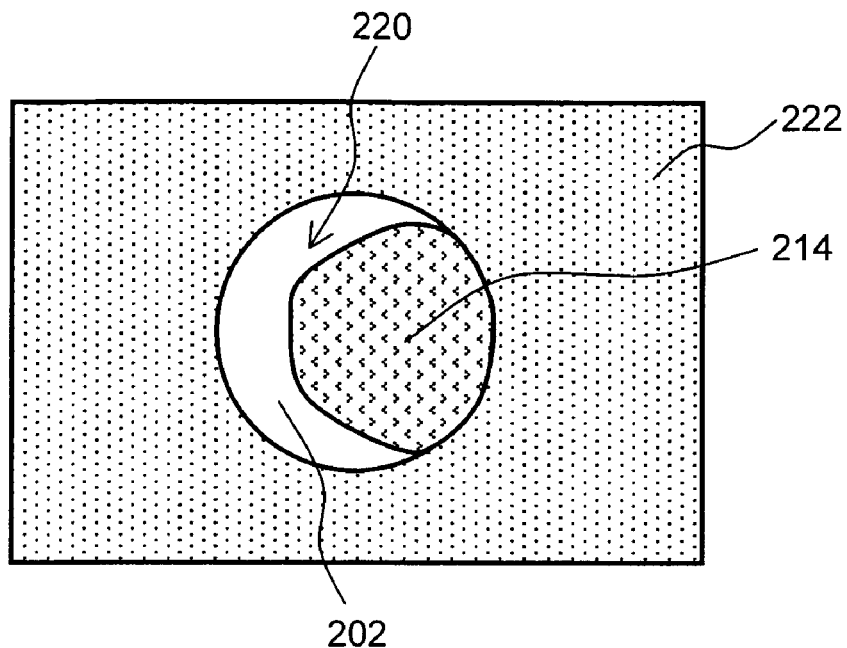
FIGS. 7A and 7B show images obtained without and with an aperture filter, respectively.

FIG. 7A shows in schematic form an image obtained without an aperture filter, and it should be noted that this information was obtained by a combination of the structures and elements shown in FIGS. 1 and 6. It should also be noted that the structure was prototypes with a microscope body with appropriate modifications and that the dielectric layer did not include dopants. A band pass filter was placed in front of the camera used to take an image of the fluorescent signal from the mocrovia hole and the bulk material surrounding the microvia. An aperture was then used to block the path of the signal from the material surrounding the microvia and a second image was taken, with the two images then being compared by an appropriate computer program, such as those commercially available. It should be noted that a change in aperture or the use of a HOE/DOE aperture allows the signal from the bulk material areas to be eliminated, but the signal from the bulk material area is used in some views to allow more accurate detection of the top edge of the microvia.

Figure 7B:
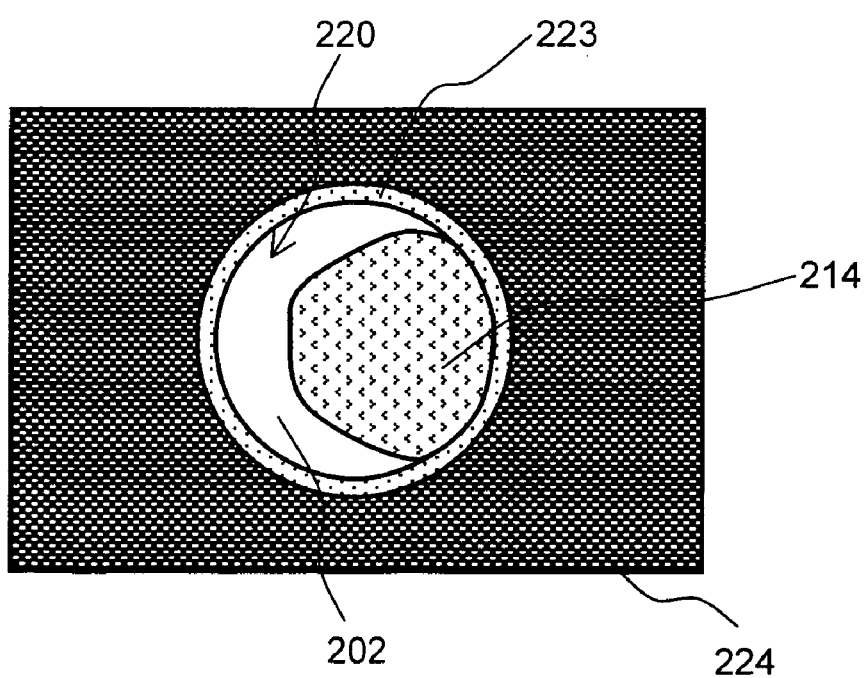

FIG. 7B shows in schematic form how an image with an aperture filter enhances various attributes of the defects or areas of interest for inspection.

Figure 8:
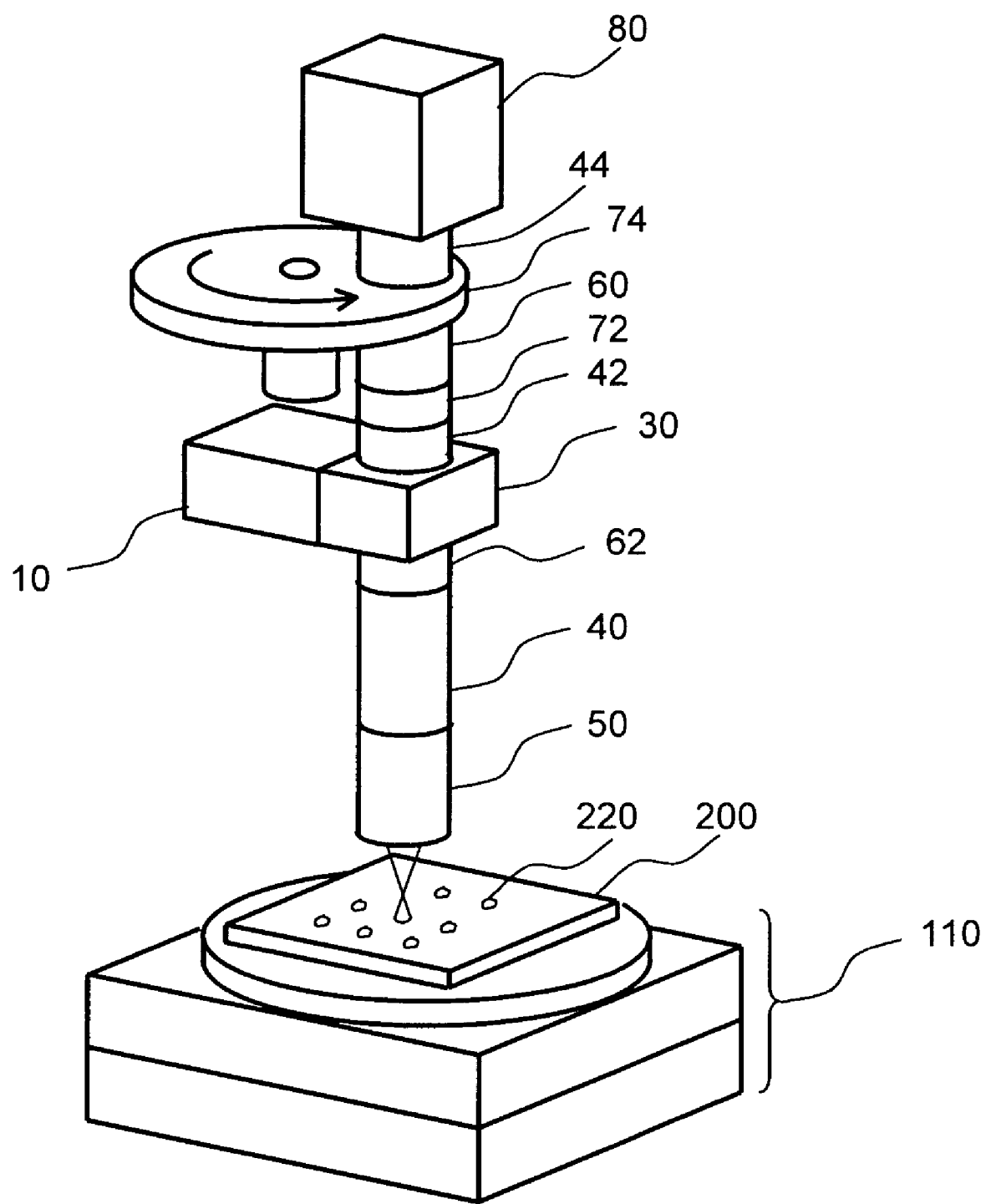
FIG. 8 illustrates a coaxial illuminator system with a high speed indexing filter wheel.

FIG. 8 illustrates a coaxial illuminator system with a high speed indexing filter wheel 74.

In this regard, high speed indexing wheel 74 is a motorized rotary indexer and the illuminator is a coaxial multi-HILED source with coaxial UV and IR sources. The illuminator may also be implemented by means of prism based illumination techniques to allow the combination of various illumination wavelengths, such as by using a beam splitter in conjunction with a Penta Prism and Rhomboid prism assembled to form a dual wavelength coaxial illumination head that can attach to existing coaxial tubes used for scope tubes.

In a present embodiment, illuminator 10 generated illumination frequencies in the range of 268 nm to 500 nm, with a CW 532 nm source providing UV to green frequencies and even a frequency at 1064 nm, which is in the near IR band, It is also possible to employ an 850 nm source, which is in the red band.

Figure 9:
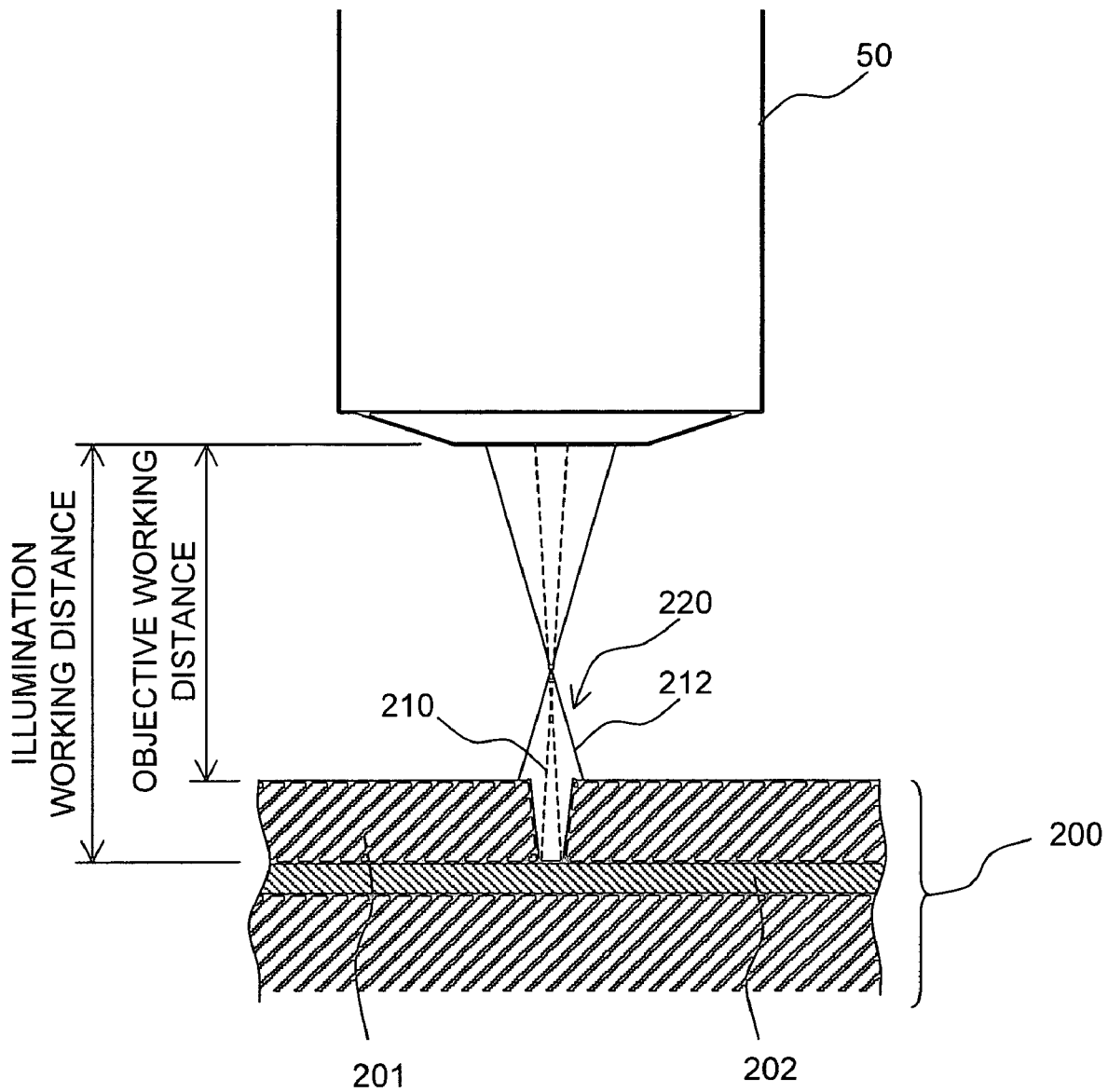
FIG. 9 illustrates a collinear image and illumination.

FIG. 9 shows how the final objective will incorporate the coaxial illumination as well as the imaging of the emission or back reflection from the dielectric or defects being inspected.

The schematic diagram is descriptive, however it should be noted that the imaging cone 212 and illumination cone 210 angled can be designed to share the same focal or imaging plane. In many cases it is useful for the imaging objective to have a field of view 212 slightly larger than the coaxial illumination field of view 210.

In this regard, FIG. 9 illustrates how the imaging side of the scope can be limited in field of view to the desired area. The illumination, however, can be larger than the imaging field of view to allow for a more uniform illumination field and, for this purpose, it has been found useful to use different sized imaging and illumination cones.

Figure 10:
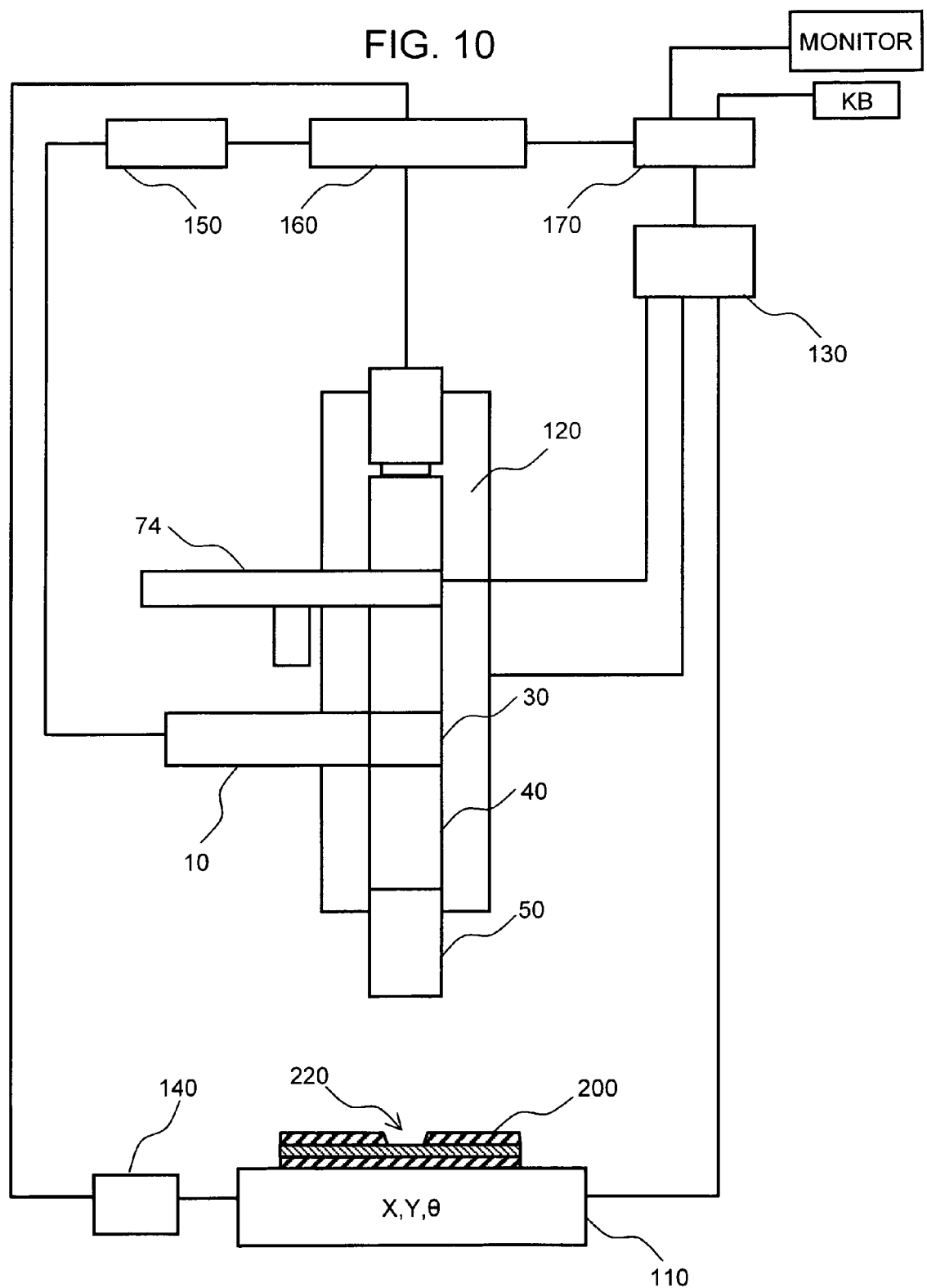
FIG. 10 illustrates a basic system and control architecture.

FIG. 10 shows a schematic of the basic system and control architecture. The key to this system is the synchronization of the motion system which carries the part to the frame grabbing software to allow for either step and repeat imaging or imaging on the fly. The output encoder 140 signal from the stages 110 will be fed into a DSP based control synchronization system which will be able to handle large amounts of data and provide a signal to synchronize the frame grabbing board 160 to the motion of the stages. The high speed vision frame grabbing card 160 will incorporate specialized vision and comparison codes in both processor memory as well as specialized function directly onto Digital Signal Processor "DSP" level processors.

Figure 11:
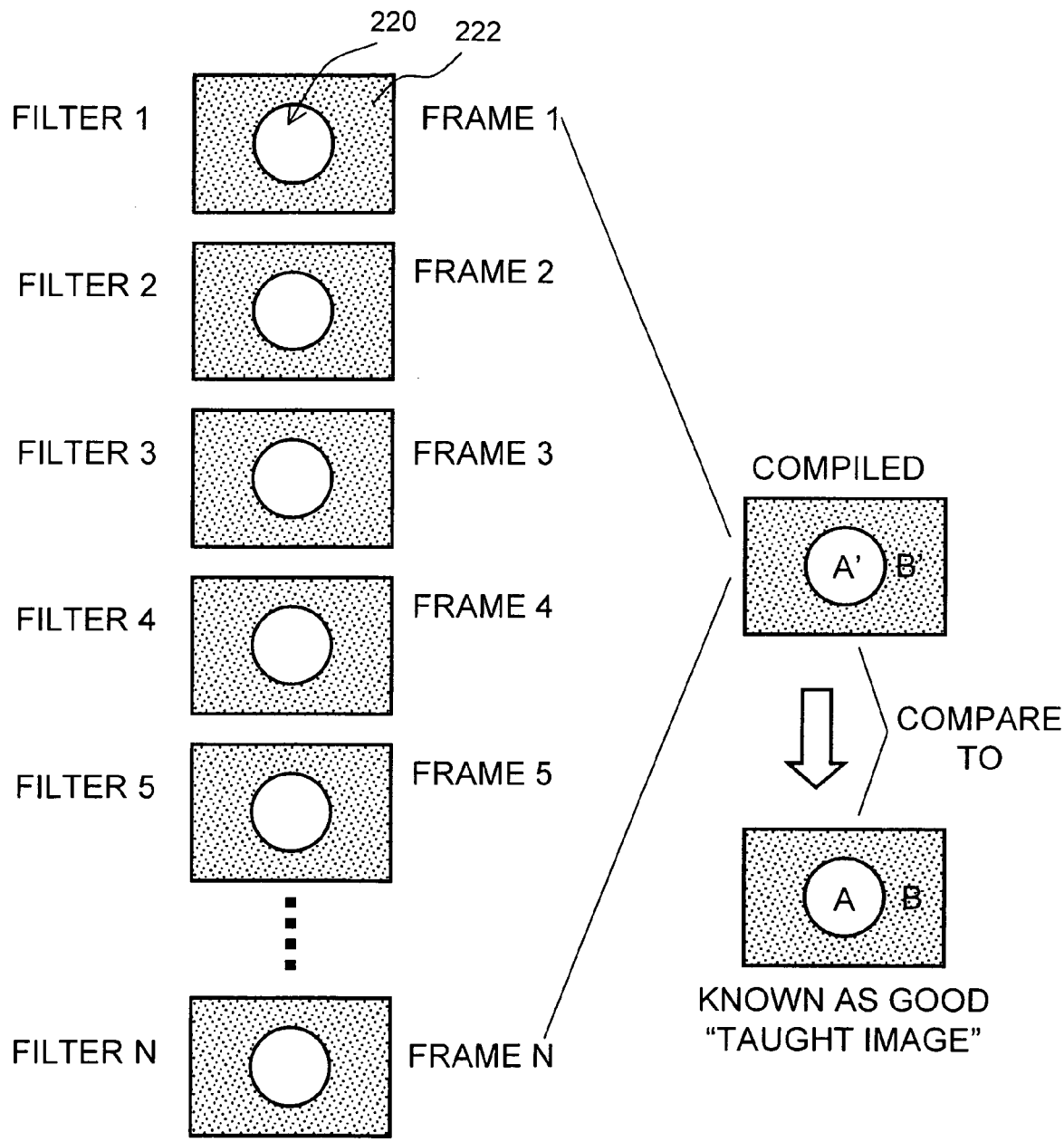
FIG. 11 shows a series of frames taken with different filters for an inspecting hole.
Figure 12:
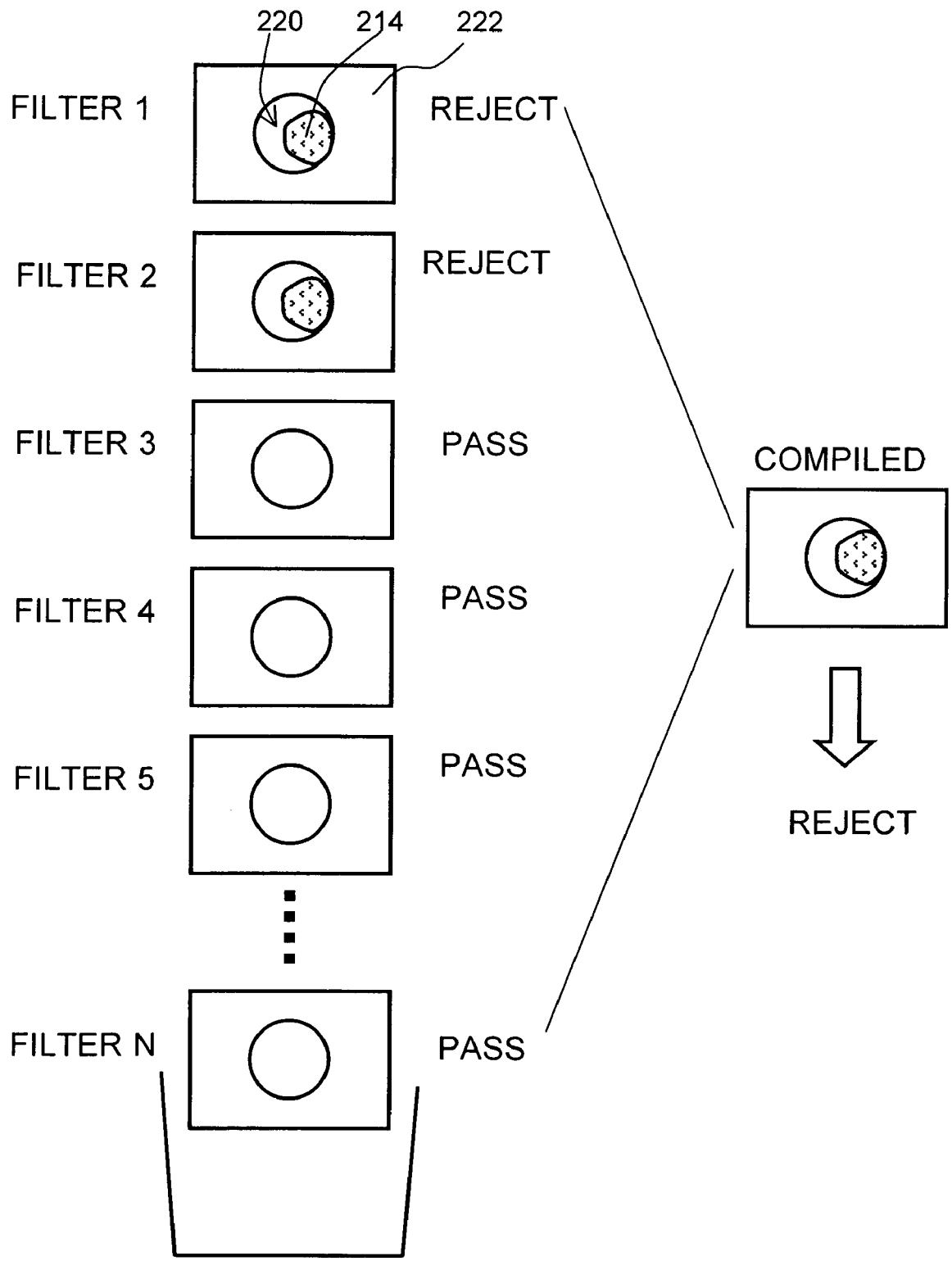
FIG. 12 illustrates a multi-frame imaging sequence visualizing of the present technique with the use of variable filters

FIGS. 11 & 12 show how the high speed frame grabbing imaging system can take a series of individual frames, each with a specific filter or illumination wavelength and then compile them into a composite image to differentiate the defects that need to be detected from the bulk surrounding material. By compiling a series of frames taken with different filters and or illumination wavelength parameters allows the defects to be found and isolated. This type of approach also provides a level of redundancy to ensure that the defects that are found are real, by direct comparison to a known good standard, it is also possible to use the compilation of frames to determine the amount of material or defects present at the bottom of a microvia or other feature being inspected.

FIG. 11 schematically shows how the system can take a series of image frames, having each frame taken at differing illumination parameters and filter/polarization settings. Each frame is then either combined together to create a composite image to emphasis the defects or left over material remaining on the conductor surface of the microvia or feature being inspected or each frame can be compared to its specific known standard on the DSP or processor level and a Pass "P"/Reject "R" is generate for each image, the software then looks at the list and fails the microvia if an "R" is on the list. This allows multiple levels of redundancy to ensure that false negatives and false positives do not occur. In essence the system performs a series of different image analysis techniques to determine the quality of the microvia or feature being observed.

In this regard, it should be noted that the information for FIG. 11 was obtained by use of the elements illustrated in FIGS. 1 and 6 and by the automated process illustrated in FIGS. 3 and 8. It should also be noted that the dielectric layer did not include fluorescent dopants, but that dopants can be used to shift the fluorescent emission wavelength. This process was performed using individual filters for a specific dead band of fluorescent emission as well as the reflectance of the UV illumination off of the copper pad. The testing was specific to UV and white light and the number of frames or pictures that can be created depends on the illumination wavelengths and filter that are used.

It should also be noted with respect to the terms appearing in FIG. 11 that "frame"="picture", a "filter" can be a band pass filter that blocks all light except light in the specific frequencies of interest, that "compiled frames" refers to stacking all of the pictures to show hidden detail, and that a "known good image" or "taught image" is the frame used to compare the compiled captured frames and is, typically and in general, an image for a GO/NO GO test.

FIG. 12 shows a multi frame imaging sequence in schematic form to allow visualization of the technique in the case of varying filters only. It should be understood the same series of images could be taken by varying the filters, illumination wavelengths, polarization, interference technique and apertures. The key is to provide levels of redundant methods to enhance and differentiate the critical defects from just noise caused by illumination. In standard industry AOI systems that use flood techniques they are limited to one specific image type and lack the ability to limit and isolate off axis illumination. In most cases they do not have coaxial illumination.

With regard to FIGS. 11 and 12, it should be noted that FIGS. 11 and 12 illustrate the difference between "good" results and "bad" results when frames are taken and compiled and that FIGS. 11 and 12 with obtained in the same manner, that is, with a non-doped dielectric layer and by taking the frames or pictures with various filters that limited the signal or that enhanced certain features of the picture or frames.

Figure 13:
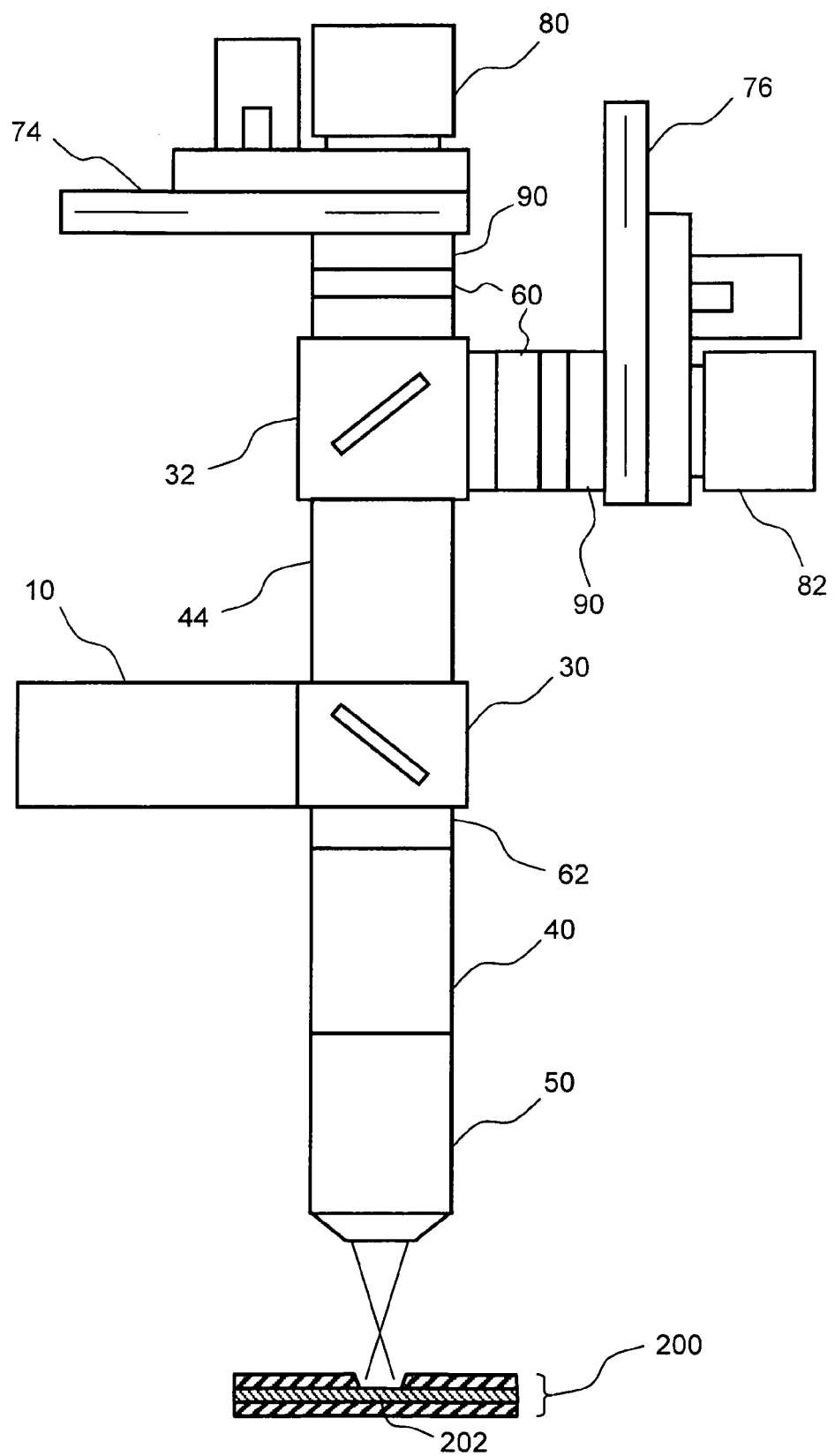
FIG. 13 is a diagrammatic representation of an optical imaging scope incorporating two cameras taking simultaneous images a different magnifications.

FIG. 13 shows in schematic form a optical imaging scope system which incorporates two CCD cameras 80, 82 so that two pictures can be taken, one at a first magnification and one at a second magnification. This allows the system to rapidly change field of view for specific features being inspected, such as variable microvia sizes or to switch between observing fiducials and the other for inspection. This provides a possibility to align every part on an array of parts on the board to ensure higher quality, taken into account growth and variability of PCB boards, especially multilayered board or flex circuits.

It should be noted with regard to FIG. 13 that a filter blocks certain light from entering the cameras and that a filter aperture filters a specific band of light only around the clear aperture, that is, where the hole is. It should also be noted that the illuminator may provide single or multiple wavelengths and that the process requires that the system operate with those specific wavelengths that work well with the material. With epoxy, for example, a white light source in combination with the UV source is acceptable. However, the addition of an IR source to the UV and white light sources provides better images of copper pads.

Figure 14:
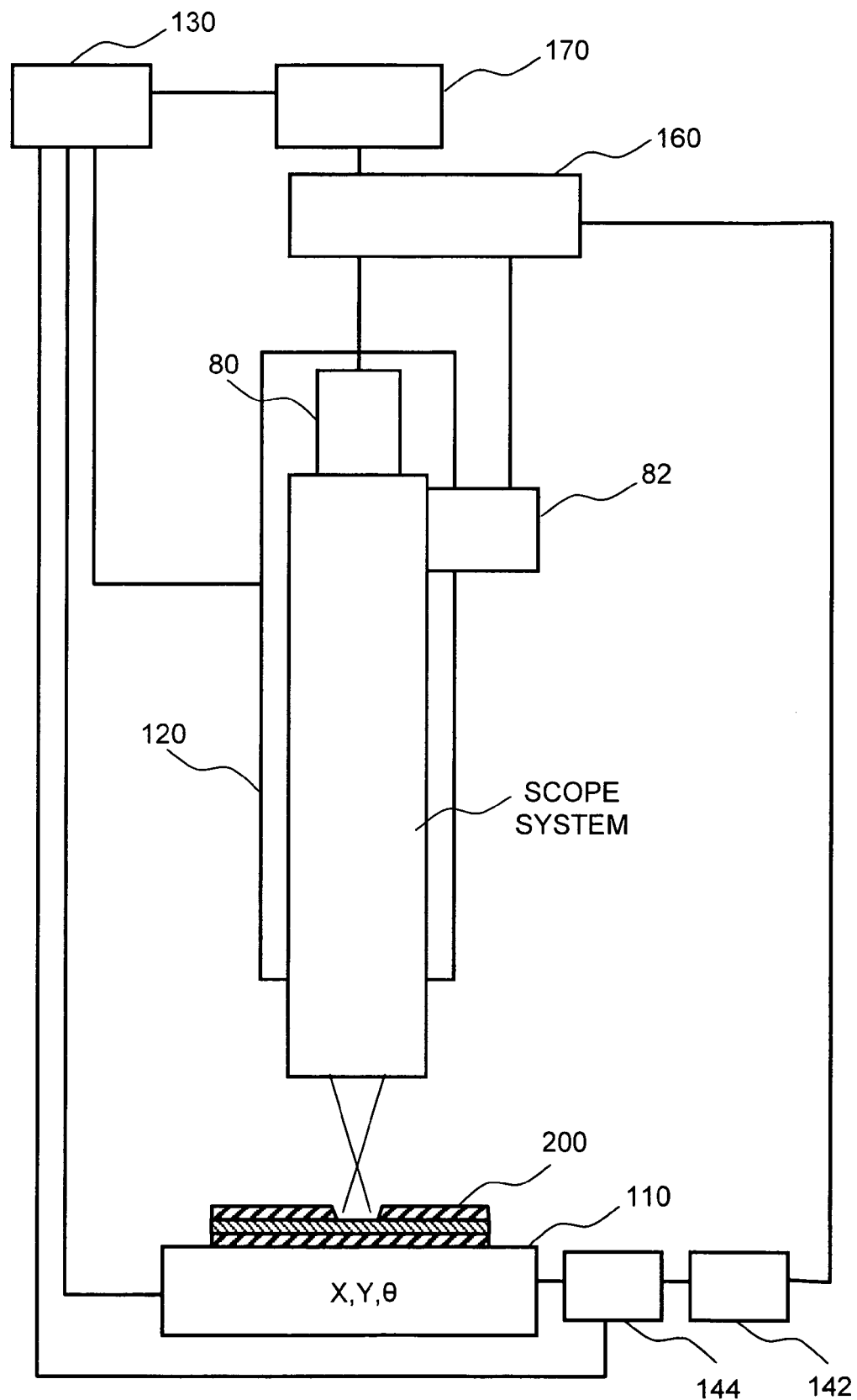
FIG. 14 is a schematic diagram of the two camera control system

FIG. 14 shows in schematic form the two camera control diagram.

As regards the terms and reference numerals appearing in FIG. 14, it should be noted that:

Motion control/synchronization card 130 takes the control signals from the motion, encoder, etc and synchronizes the sequences;

Control CPU 170 performs a system supervisory role and provides the GUI interface)

Vision Card/Frame Grabber 160 controls synchronization with the DSP signal feed, which is slaved off of the encoder;

the CCD cameras (CCD or Enhanced CCD imaging cameras are indicated, respectively as elements 80 and 82;

Scope system 120 includes the illuminator, filter wheel, HOE filter, transfer optics, and so on;

element 200 is a PCB laminate or flex circuit;

element 110 is a motion table or work table;

element 144 is an encoder; and element 142 is DSP feed and data synchronization functions.

Figure 15:
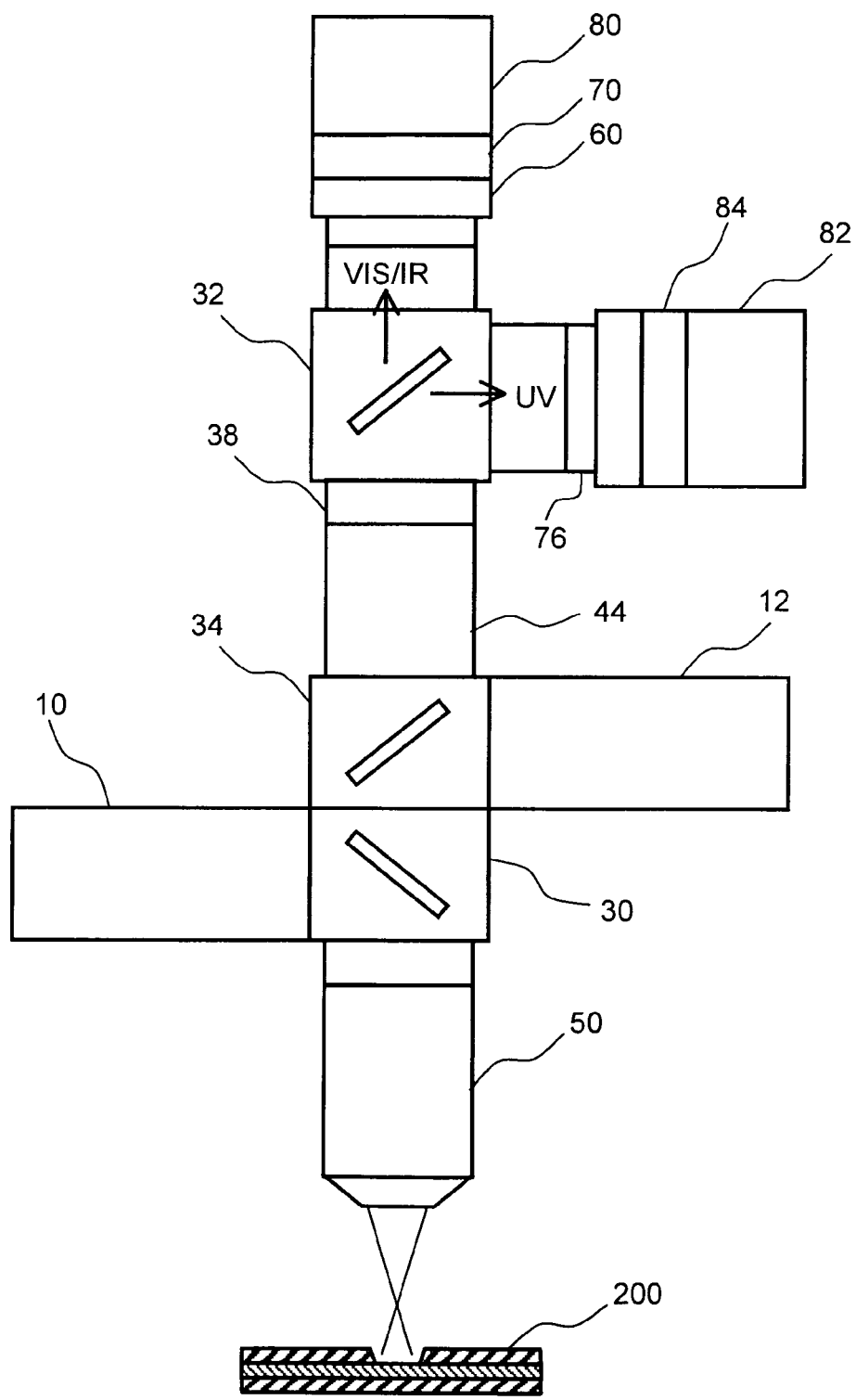
FIG. 15 is a diagrammatic illustration of the use of dual cameras and illuminators.

FIG. 15 shows in schematic form the use of dual cameras and dual coaxial illuminators. This allows variation in illumination wavelengths within a coaxial scope imaging system. Of course specialized corrective optics would need to be used to correct for each wavelength.

In this regard, it should be noted that CCD #1 is used to view the visible and IR wavelength signals and that CD #2 views only the UV signal or the fluorescent emission.

Figure 16:
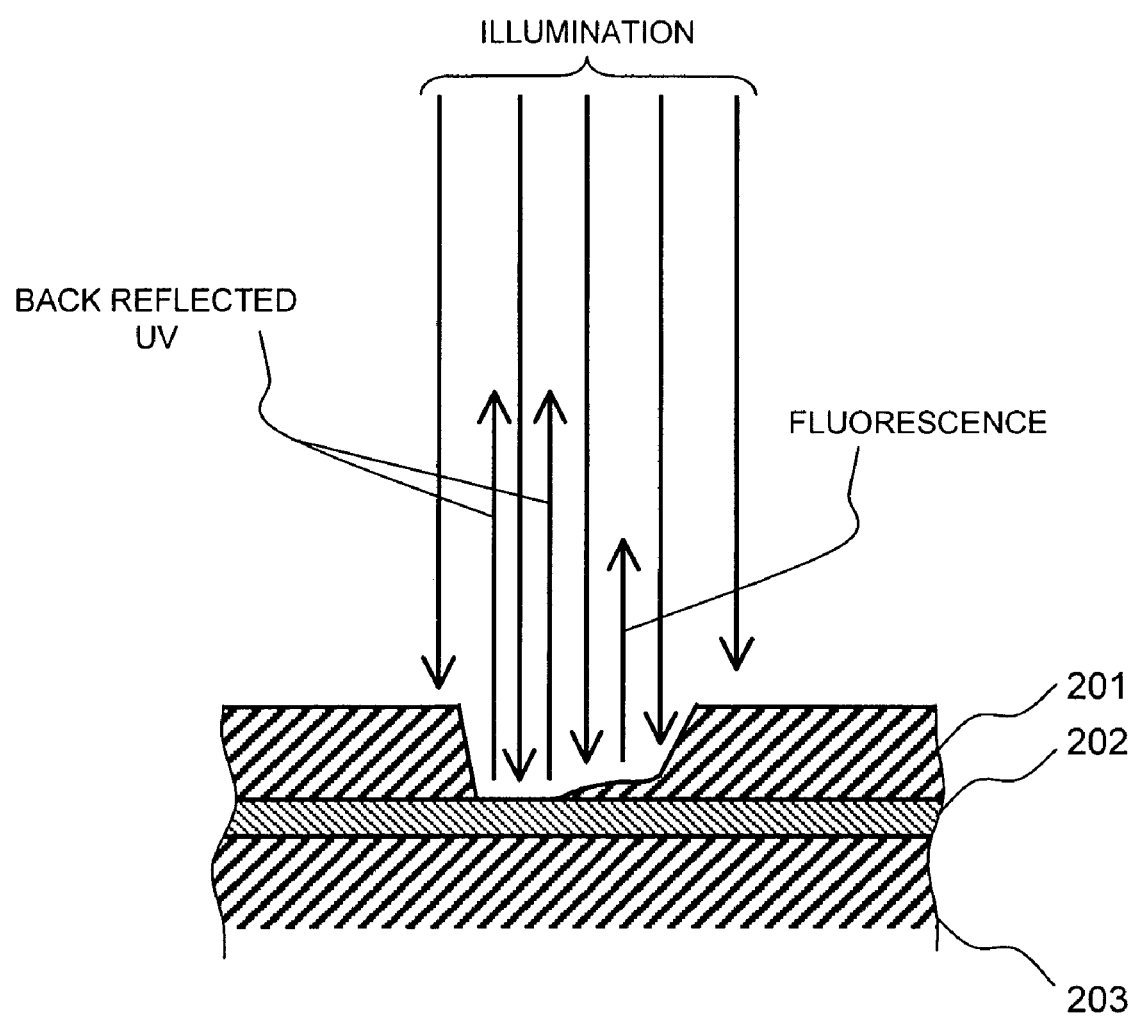
FIG. 16 illustrates the signals and images to be analyzed.

FIG. 16 shows in schematic form the types of signals and image that would need to be analyzed. The primary signal in some circumstances would be the emission "fluorescence" being emitted from the defect or thin film dielectric that is left over; the secondary might be the illuminator light that is reflected off of the conductor surface. In some cases the imaging objective might be tailored to the emission wavelength, such that the only in focus image will be that of the defects of interest.

Figure 17:
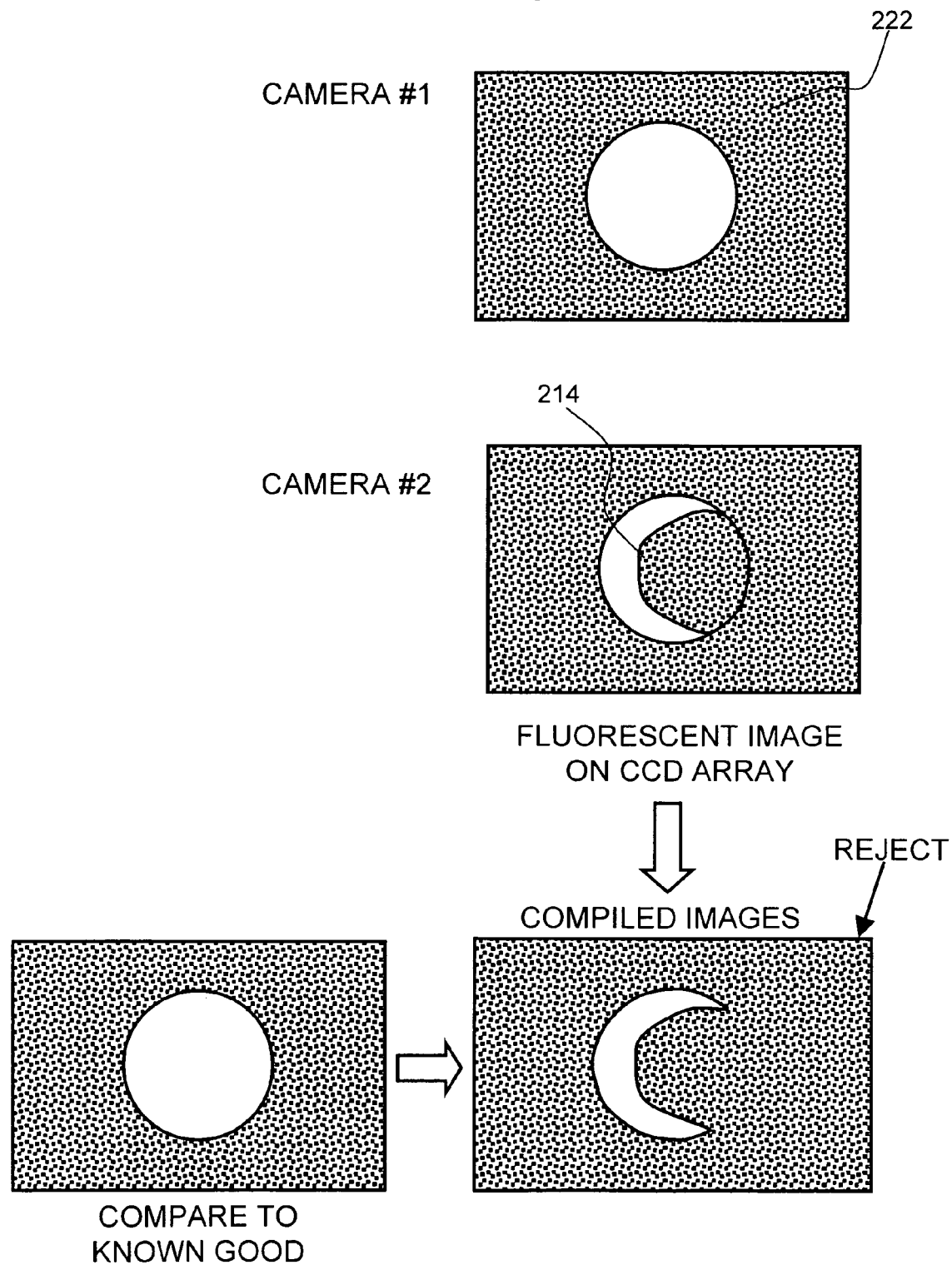
FIG. 17 illustrates the use of back reflected light to emphasize defects.

FIG. 17 shows in schematic form shows the use of back reflected light from the conductor surface and how that could be used in conjunction with the fluorescence emission image to emphasize the defects of interest.

With regard to FIG. 17, the system uses a dual camera scope with a fluorescent plate attached (glued) to the front surface of camera 2, in a manner similar to that illustrated in FIGS. 1 and 6, and that the dielectric layer did not include fluorescent dopants.

It should also be noted that the camera #1 image was obtained by illuminating the surface with UV light and taking a picture at the surface of the emission. Camera #1 utilized a band pass filter to eliminate all wavelengths except that of the fluorescent emission. Camera #2, in turn, viewed the back reflection of the UV source light off of the copper pad and a band pass filter was used to only allow the UV to return back to camera #2 imaging array, which was covered by a green fluorescent plate that glows green when illuminated by UV light. The returning UV light was imaged to the surface of the fluorescent plate and the CCD pixels captured the reflected portion which represented the copper pad that was showing. In this case as an example a crescent shape. The two images are superimposed on each other to reveal the small island of material that still covers the bottom of the microvia.

Figure 18:
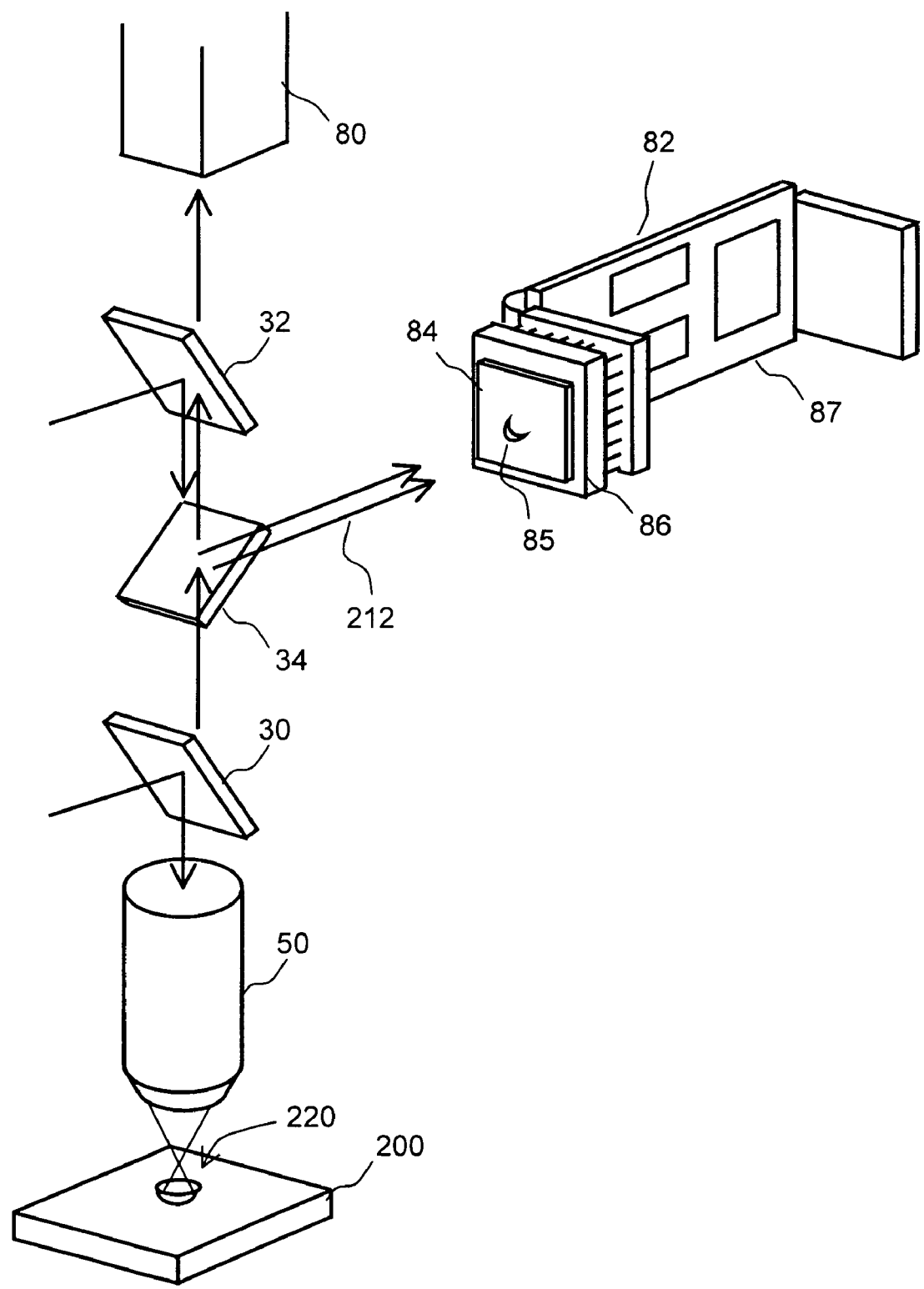
FIG. 18 illustrates a fluorescent glass plate attached to a CCD or EMCCD.

FIG. 18 shows in schematic form how a fluorescent glass plate can be attached to a CCD or EMCCD array to transform incoming back reflected UV light into visible spectra at the array.

FIG. 19 shows pictures of the types of fluorescent glass being illuminated by UV light and its respective emission wavelength.

Figure 20A:
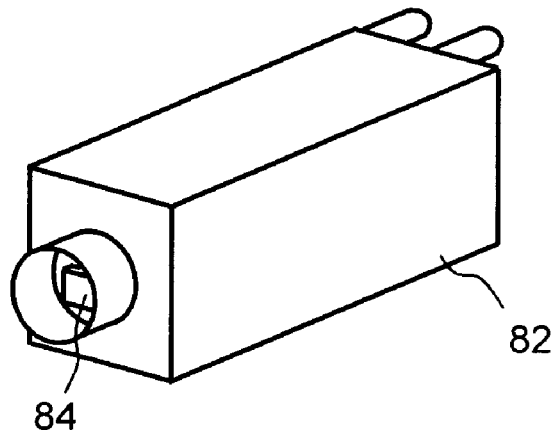
FIG. 20 illustrates the integration of fluorescent glass into a CCD or EMCCD.
Figure 20B:
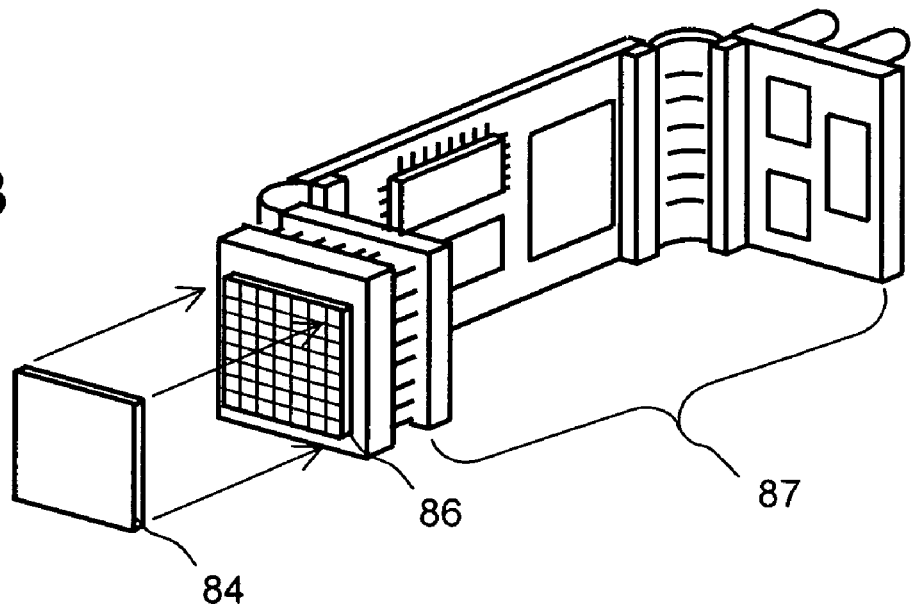

FIG. 20 shows in schematic form the integration of fluorescent glass onto a CCD or EMCCD device.

Figure 21:
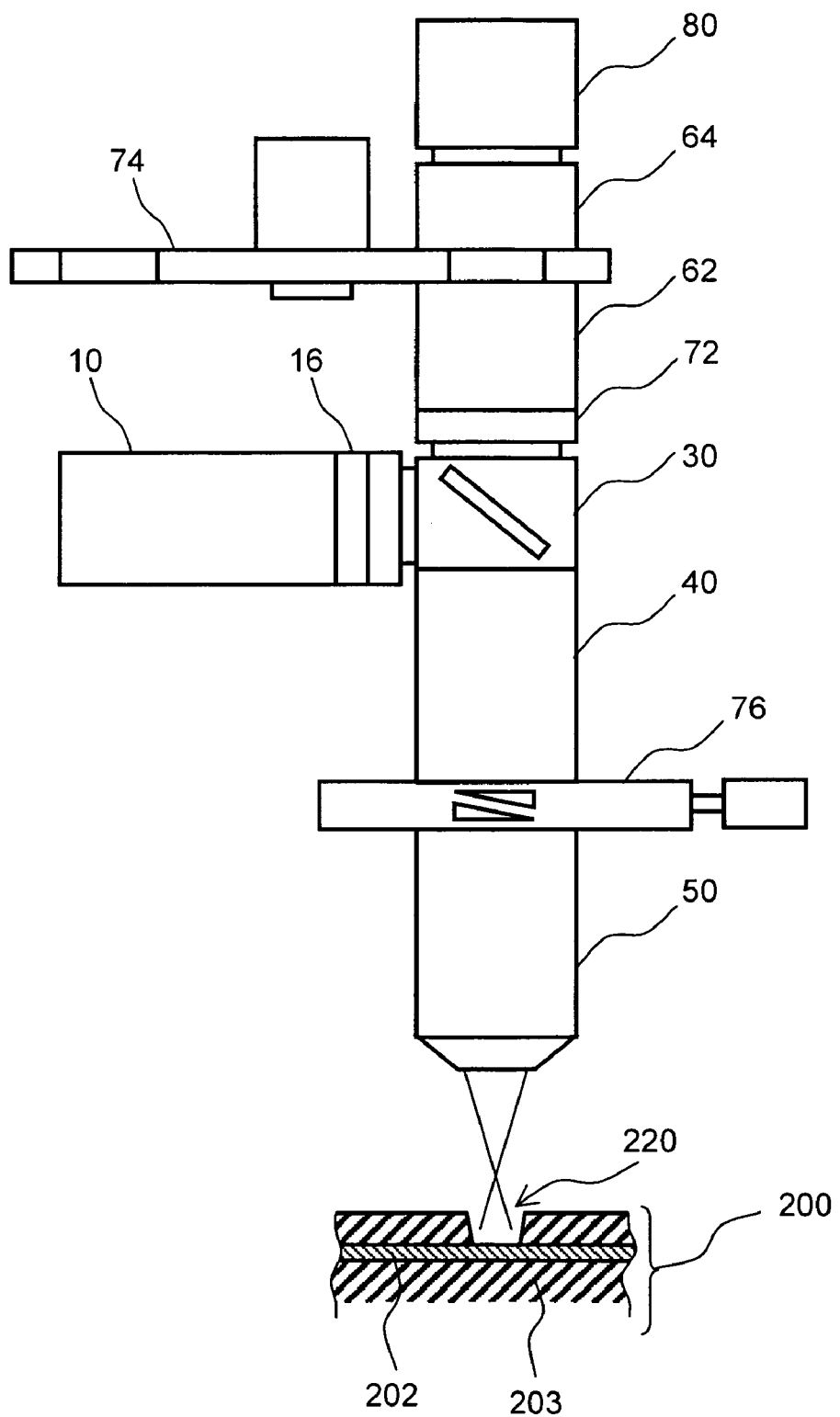
FIG. 21 illustrates the use of a differential interference contrast prism.

FIG. 21 shows in schematic form the use of a differential interference contrast prism assembly prior to the final objective to provide further enhancement of the defects being observed. This provides a simple method of creating a phase contrast to boost the image of the emission being emitted by the defects. The addition of phase contrast imaging provides a significant capability to the overall system by allowing further differentiation of the bulk surrounding material from the specific defects or left over dielectric material on the conductor pad or features being observed.

With regard to FIG. 21, the "differential interference contrast prism assembly" employs a hybrid reflected light method. The hybrid reflected light method is a well known technique applied in the examination of opaque materials that are usually highly reflective and that therefore do not absorb or transmit a significant amount of the incident light. Slopes, valleys, and other discontinuities on the surface of the pad at the bottom of the microvia create optical path differences, which are transformed by reflected light differential interference contrast technique into amplitude or intensity variations that reveal a topographical profile (surface roughness or residual material). Unlike the situation with transmitted light techniques or simple imaging, the image created in reflected light differential interference contrast can often be interpreted as a true three-dimensional representation of the surface geometry. In our case, this allows us to visualize further potential defects.

FIG. 22 shows a picture of the scope system and the DIG module, polarizer indexer slider and the coaxial illuminator port. The Objective is a custom 20× Nikon objective, with quartz optics for use in the UV.

It should be noted that the elements shown in FIG. 22 include, as discussed previously herein:
    80=CCD Camera
    64=Filter/conditioning optics
    74=High Speed Filter Wheel
    62=Transfer optics
    72=Holographic Filter
    10=Illuminator
    16=Polarizer
    30=Beam Splitter
    40=Scope Tube
    76=Differential Interference Contrast Module
    50=Objective; and;
in the picture
    80=CCD Camera (Picture shows the C-mount for the camera/no camera shown)
    64=Filter/conditioning optics (As shown on the picture)
    74=High Speed Filter Wheel (no filter wheel)
    62=Transfer optics (embedded in the tube scope)
    72=Holographic Filter (No used)
    10=Illuminator (The picture shows illuminator port)
    16=Polarizer (Picture shows it at the port for illumination)
    30=Beam Splitter (picture shows just after the polarizer)
    40=Scope Tube (picture shows scope tube)
    76=Differential Interference Contrast Module (picture shows DIC module as noted)
    50=Objective (Picture/as shown)

Figure 23A:
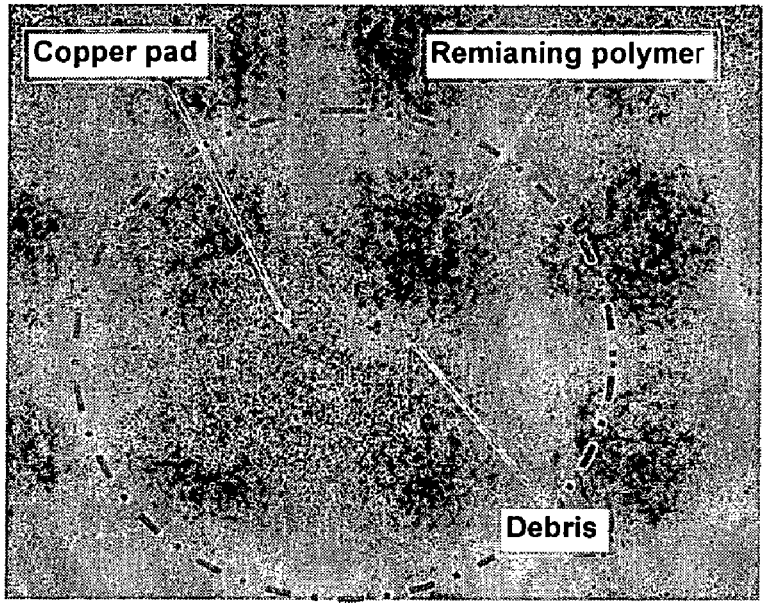
FIGS. 23A and 23B are respectively illustrations of an image of a microvia and a corresponding fluorescent image of the microvia; and, FIGS. 24A and 24B are respectively a gray scale image and a color enhanced image of a microvia using the apparatus and method of FIG. 6.
Figure 23B:
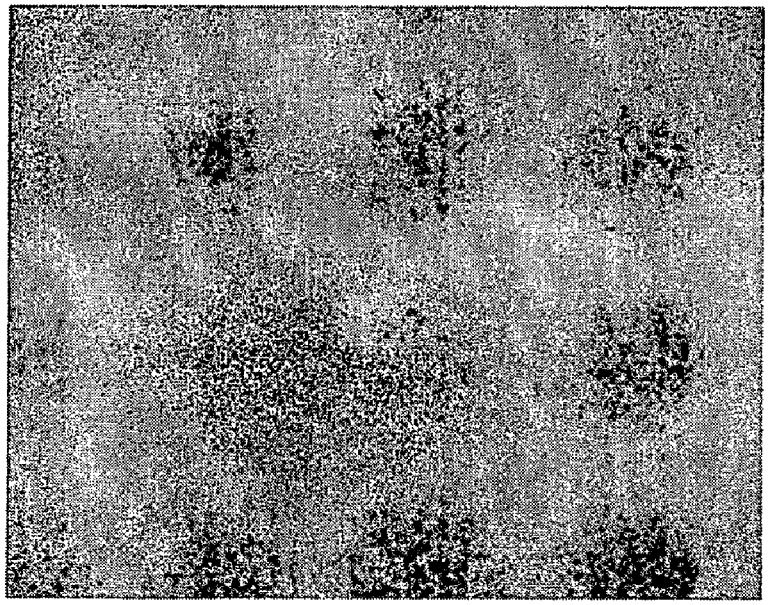
Figure 24B:
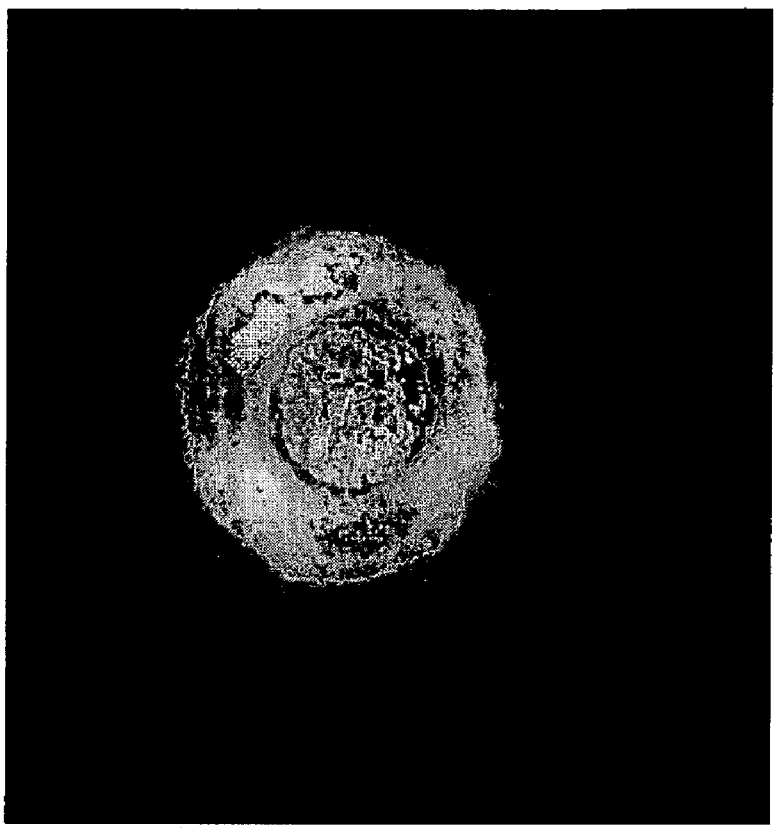
Figure 24A:
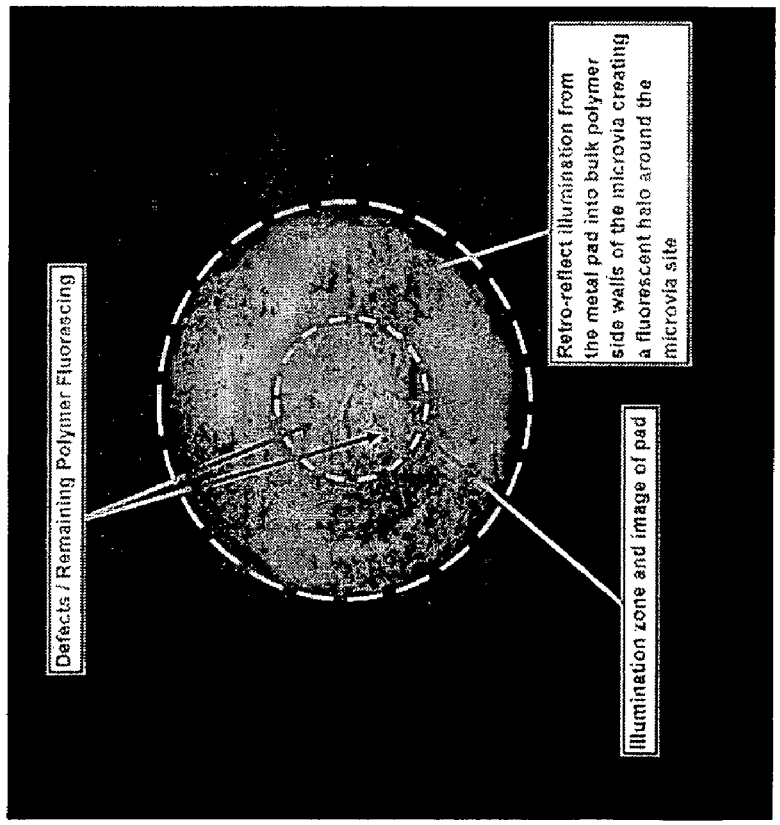

Lastly, FIGS. 23A and 23B are respectively illustrations of an image of a microvia and a corresponding fluorescent image of the microvia and FIGS. 24A and 24B are respectively a gray scale image and a color enhanced image of a microvia using the apparatus and method of FIG. 6, all according to the present invention.

In conclusion, while the invention has been particularly shown and described with reference to preferred embodiments of the apparatus and methods thereof, it will be also understood by those of ordinary skill in the art that various changes, variations and modifications in form, details and implementation may be made therein without departing from the spirit and scope of the invention as defined by the appended claims.

What is claimed is:

1. An apparatus for inspecting a laser drilled blind hole, comprising:
    an illuminator for illuminating the blind hole with at least UV light,
    an objective lens for imaging the blind hole at a CCD, whereas the CCD for converting the images to electric signals,
    an indexing filter wheel for making images of fluorescent light emitted from the blind hole at a plurality of wavelengths, a vision card for grabbing the electrical images as frames, and a CPU for comparing the image frame to a predetermined good image at each wavelength.

2. An apparatus for inspecting laser drilled blind holes in a printed circuit board, comprising:

an X-Y-Z stage for mounting the printed circuit board, an illuminator for illuminating the blind hole with at least UV light, an objective lens for imaging the blind hole at a CCD, whereas the CCD for converting the images to electric signals, an indexing filter wheel for making images of fluorescent light emitted from the blind hole at a plurality of wavelengths, a vision card for grabbing the electrically converted images as frames, a CPU for comparing the image frame to a predetermined good image at each wavelength, and a motion control for controlling the X-Y-Z stage, the indexing filter wheel with commands from the CPU.

\* \* \* \* \*